United States Patent [19]

Ivarsson et al.

[11] Patent Number: 5,313,264
[45] Date of Patent: May 17, 1994

[54] OPTICAL BIOSENSOR SYSTEM

[75] Inventors: Bengt Ivarsson, Bälinge; Jönsson Ulf, Upsala; Stefan Sjölander, Upsala; Ralph Ståhlberg, Upsala; Hakan Sjödin, Uppsala, all of Sweden

[73] Assignee: Pharmacia Biosensor AB, Upsala, Sweden

[21] Appl. No.: 681,533
[22] PCT Filed: Nov. 9, 1989
[86] PCT No.: PCT/SE89/00641
 § 371 Date: May 10, 1991
 § 102(e) Date: May 10, 1991
[87] PCT Pub. No.: WO90/05295
 PCT Pub. Date: May 17, 1990

[30] Foreign Application Priority Data

Nov. 10, 1988 [CH] Switzerland ............. 8804075-3

[51] Int. Cl.$^5$ ............... G01N 21/17; G01N 33/53
[52] U.S. Cl. ............. 356/73; 250/458.1; 356/318; 356/446; 356/246; 356/445
[58] Field of Search .......... 356/73, 317, 318, 338, 356/343, 417, 446, 246, 445; 250/458.1, 459.1, 461.1, 461.2

[56] References Cited

U.S. PATENT DOCUMENTS 4,304,257 12/1981 Webster .

FOREIGN PATENT DOCUMENTS

| | | |
|---|---|---|
| 0067921 | 6/1981 | European Pat. Off. . |
| 0202021 | 11/1986 | European Pat. Off. . |
| 0226470 | 12/1986 | European Pat. Off. . |
| 0254430 | 6/1987 | European Pat. Off. . |
| 0278577 | 2/1988 | European Pat. Off. . |
| 0257955 | 3/1988 | European Pat. Off. . |
| 0286195 | 10/1988 | European Pat. Off. . |
| 0305109 | 3/1989 | European Pat. Off. . |
| 05417 | 6/1989 | PCT Int'l Appl. . |
| 2197065 | 5/1988 | United Kingdom . |
| 2197068 | 5/1988 | United Kingdom . |

OTHER PUBLICATIONS

"A Compact Surface Plasmon Resonance Senso for Measurement of Water in Process" K. Matsubara, et al vol. 2, No. 8, 1988.
"Optical Chemical Sensor Based on Surface Plasmon Measurement" K. Matsubara, et al. vol. 27, No. 6, Mar. 15, 1988.
"Internal Reflection Spectroscopy: Review and Supplement" F. Mirabella, Jr., et al. 1985.
"Reflectometry as a Technique To Study the Adsorption of Human Fibrinogen at the Silica/Solution Interface" P. Schaaf, et al, Langmuir 1987.
"Polymer Concentration Profile Near a Liquid-Solid Interface: Evanescent Wave Ellipsometry Study" M. W. Kim, et al, Macromolecules 1989.

(List continued on next page.)

Primary Examiner—F. L. Evans

[57] ABSTRACT

An optical biosensor system using internal reflection versus angle of incidence determination for the detection of biomolecules, the system comprising a sensor unit (10) with at least two sensing surfaces (39A-D), a source of light (1), and lens means (2) for forming a convergent beam of light which is focused in wedge-shape fashion to form a streak of light (5) extending transversely over all the sensing surfaces; a photodetector device (7) in the form of a two-dimensional matrix of individual photodetector; optical imaging instrumentation in the form of an anamorphic lens system (6) for the purpose of imaging rays of reflected light from the sensing surfaces on each its own column of photodetectors, so that for each sensing surface there is a corresponding set of columns of photodetectors; and an evaluation unit (8) for determining the minimum reflectance or the resonance angle at each of the sensing surfaces. The invention also relates to a method for calibrating the biosensor system, a method for correcting for baseline drift as well as a method for temperature regulation of thermostat means in the biosensor system.

53 Claims, 12 Drawing Sheets

OTHER PUBLICATIONS

"A New Immunoassay Based on Fluorescence Excitation by Internal Reflection Spectroscopy" M. N. Kronick, et al, Journal of Immunological Methods, (1975).

"Total Internal Reflection Fluorescence: A Technique for Examining Interactions of Macromolecules with Solid Surfaces" B. K. Lok, et al, Journal of Colloid and Interface Sciences, vol. 91, No. 1, (1983).

"Evanescent Detection of Adsorbed Protein Concentration-Distance Profiles: Fit of Simple Models to Variable-Angle Total Internal Reflection Fluorescence Data" W. M. Reichert, et al Applied Spectroscopy vol. 41, No. 3, (1987).

"Physics of Thin Films" H. Raether, et al Academic Press 1977.

"Surface Plasmon Resonance For Gas Detection and Biosensing" B. Liedberg, et al Sensors and Actuators (1983).

"The ATR Method With Focused Ligth-Application to Guided Waves on a Grating" E. Kretschmann Optics Communications vol. 26, No. 1 (1978).

"Angular Emission Profiles of Dye Molecules Excited by Surface Plasmon Waves at a Metal Surface" R. Benner, et al Optics Communication vol. 30, No. 2, (1979).

"Plasmon Surface Polariton Dispersion by Direct Optical Observation" J. D. Swalen, et al Am. J. Phys. (1980) vol. 48, No. 8.

"Flow Injection Analysis From Test Tube to Integrated Microconduits" Ruzicka Analytical Chemistry, vol. 55, No. 11 1983.

FIG. 1(A) VALVE OPEN

FIG. 1(B) VALVE CLOSED

OPTICAL BIOSENSOR SYSTEM

The present invention relates to an optical multi-analyte biosensor system employing the principle of internal reflection of polarized light for use in biological, biochemical and chemical analysis and in particular for detecting a specific molecule, for example antigens. The detection method used in the biosensor system may be based on the evanescent wave phenomenon at total internal reflection, such as surface plasmon resonance (SPR), critical angle refractometry, total internal reflection fluorescence (TIRF), total internal reflection phosphorescence, total internal reflection light scattering, and evanescent wave ellipsometry. Furthermore, the detection method may be based on Brewster angle reflectometry.

The main advantage of the internal reflection based techniques is that the sensitivity region for the specific substance is restricted to the extension length of an evanescent wave, i.e. the depth of an electromagnetic wave penetrating into the liquid medium from the sensing surface side. Consequently, there will be a minimum of influence on the response connected to specifically bound analyte molecules from non-bound sample molecules. Moreover, the penetration depth of the evanescent wave for a totally reflected ray of light depends on the angle of incidence for the ray. For a comprehensive treatment of the concept of internal reflection one is referred to Mirabella and Harrick, Internal Reflection Spectroscopy, Harrick Scientific Corporation, N.Y. 1985.

The optical response induced by either the primary evanescent wave, or by a secondary evanescent wave excited in turn by said primary evanescent wave, may be measured as changes in the reflectance or in the state of polarization of the incident light wave upon reflection, or as the fluorescence or phosphorescence or light scatter of radiation, as a result of a specific substance interaction with a sensing layer at the sensing surface.

The optical response related to the specific substance may be measured as the reflected intensity as a function of angle of incidence of p-polarized light, being applicable for surface plasmon resonance, Brewster angle reflectometry, and critical-angle refractometry, in that the angle of minimum reflectance is determined and related to a refractive index and surface concentration of the bound substance at the sensing surface.

With regard a detection using surface plasmon resonance, this will be treated in more detail hereinafter.

Internal multiple-angle Brewster angle reflectometry, based on rotating optical means and a rotating prism for the variation of incident angle, has been shown to provide information to characterize the adsorption of proteins on a silica prism/solution interface; see Schaaf, P. et al. Langmuir, 3, 1131–1135 (1987).

Critical-angle refractometry has so far been used mainly to measure the concentration or density of solutions in process streams.

In a detection employing evanescent wave ellipsometry, the optical response related to the specific substance is measured as changes in the state of polarization of elliptically polarized light upon reflection, in that this state of polarization is related to a refractive index, thickness, and surface concentration of a bound sample at the sensing surface. Multiple-angle evanescent wave ellipsometry, in the form of using rotating optical means and a rotating prism for the variation of incident angle, and a phase-modulated ellipsometer, has been used for studying the polymer (polystyrene) concentration profile near a prism/liquid interface; see Kim, M. W., Macromolecules, 22, (1989) 2682–2685. Furthermore, total internal reflection ellipsometry in the form of stationary optical means at a single angle of incidence has been suggested for quantification of immunological reactions; see EP-A1-0 067 921 (1981), and EP-A1-0 278 577 (1988).

By a detection employing evanescent wave excitation fluorescence through an angle of incidence dependent TIRF, the intensity and wavelength of the radiation emitted from the either natively fluorescent or fluorescence labeled sample molecules within the sensing layer is measured. Total internal reflection fluorescence (TIRF) was suggested for a immunoassay in 1974, in that a separate antigen-coated quartz slide was brought into optical contact with a quartz prism via a drop of index-matching solution and by using a Teflon O-ring sealed plexiglas cell, Kronick, M. M. et al., J. Immunol. Meth., 8, (1975) 235–240. Now total internal reflection fluorescence is an established technique to examine interactions of macromolecules with solid surfaces, the surface being generally one side of the coupling prism; see Lok, B. K. et al., J. Colloid Interf. Sci., 91, (1983) 87–103. Furthermore, variable-angle total internal reflection fluorescence has been used to study adsorbed protein concentration profiles at a prism surface; see Reichert, W. M. et al., Applied Spectroscopy, 3, (1987) 503–508.

In a detection employing evanescent wave excitation scattered light, through an angle of incidence dependent evanescent wave penetration depth, the intensity of the radiation scattered within the sensing layer due to its interaction with the specific substance is measured. Scattered total internal reflectance (STIR) has been suggested for utilization in immunoassays, and in a preferred embodiment, colloidal gold is used as a label for the solution phase immunologically active component; see EP-A2-0 254 430 (1987).

With regard to the use of surface plasmon resonance (SPR), in somewhat simplified terms SPR may be said to be a technique according to which changes in the refractive index of a layer close to a thin free-electron metal film are detected by way of consequential changes in the intensity of a p-polarized light beam reflected from the metal film (see for example Raether H, Physics of Thin Films, Academic Press, N.Y., 9 (1977) 145.

In the first publication indicating the possibilities of SPR technology in biochemical analysis, Liedberg B et al., Sensors and Actuators, 4 (1983) 299 have at first adsorbed a monolayer of IgG to a silver surface and then adsorbed to said monolayer a layer of anti-IgG, in order to then study the effect of the resultant change in the resonance angle. EP 202 021 describes a biosensor employing movable optical instrumentation for determining the angle—henceforth called the resonance angle—at which surface plasmon resonance occurs. Such movable optical units are not suitable for commercial-type instruments because (i) when readings of the resonance angle are to be taken this will require manual operations, and (ii) technical manufacturing tolerances in the suspension mechanism of the movable optical system contribute to errors occurring in the measurements of the resonance angle. EP 257 955 describes another optical system which is scanned mechanically for determining the resonance angle. GB 2 197 068 describes an optical sensor employing a divergent beam of rays for irradiating the sensitized surface, this latter being a metal film with receptors or ligands which interact selectively with one or more biomolecules. The optical system is stationary, so the above-mentioned drawbacks of movable optical systems are avoided.

A source of light is employed for irradiating a sensitized surface which is subject to the action of a sample solution while another source of light is employed for irradiating another sensitized surface which is subject to the action of a reference solution. The light sources and sensitized surfaces are arranged in such a way that the reflected divergent beams will strike a photodetector matrix. By means of alternate activations of each one of the two light sources, the resonance angle obtained from each of the two sensitized surfaces can be measured with precision, and the difference between the two resonance angles at each of the two sensitized surfaces will be a measure of the amount of the specific biomolecule bound on the sensitive layer. The disadvantage of this apparatus resides in the use of two individual sources of light—one for the reference solution, one for the sample solution—as this will tend to make the measuring result uncertain in view of the fact that the resonance angle is highly dependent on the spectral character of the light source. Another drawback of this known optical sensor resides in the positioning thereof directly on the prism of the optical system, and in having light directed to the sensitized surface via an immersion oil that has a suitable refractive index. Such a use of light-coupling oils will involve much practical inconvenience when the sensor unit, comprising a sensitized metal layer coated on a transparent plate, is to be replaced by a new sensor unit with a sensing surface having an affinity for a different specific biomolecule. The replacement operations will inevitably give rise to oil smears, and the prism has to be cleaned before a new sensing surface can be analyzed. Manipulation of the instrument will thus be a somewhat messy business. As to the actual structure of the analytical instrument, this is not disclosed in the aforesaid GB patent specification.

EP 226 470 describes an apparatus for microchemical analyses comprising two glass plates with a gel placed between them. The apparatus is of the disposable type, to be used only once. One of the two glass plates serves as a platform on which the sample liquid is applied. Capillary force will then draw the sample liquid into the capillary cell that has been formed between the plates. A device of this type, the dimensions of which are about 3×1.5 cm, requires the use of tweezers or the like for handling. It is difficult to determine the volume of the liquid sample, and this device is therefore unsuitable for quantitative analyses.

EP-A1-0 305 109 (published after the priority date claimed in the present application) describes a SPR sensor system employing a focused (fan-shaped) light beam to illuminate the sensitive surface through a curved transparent block and via an index matching fluid. The beam enters the transparent block in a direction orthogonal to the tangent of the surface of the transparent block.

As was published by Kretschmann, E., Optics Communications, 26, (1978) 41–44, the problem of slow speed of operation relative to changes in reflectance and the insufficient precision in the resonance angle determination related with SPR procedures based on moveable mechanics, is solved by the use of a fan-shaped beam (equivalent to several beams incident upon the sensor surface over a range of angles) and of collection of the reflected beams (over a range of angles) by an array of angularly spaced detectors.

Furthermore, the transparent block described in EP-A1-0 305 109 may take the form of a hemicylinder creating a wedge-shaped beam, giving a line of a small illuminated area on the sensing surface. The hemicylindrical lens has the advantage that it can be used to perform several tests simultaneously on a single sample. To this end, the sensing surface takes the form of a series of sensitive areas, each comprising a different antibody, with each separate area being monitored by its own detector in a detector array. The cylindrical focusing principle used to produce an identical angular range of light beams along a focused line for SPR of separate surface areas has been published by Benner, R. E. et al. Optics Communications 30 (1979) 145–149, and Swalen, J D et al. Am J. Phys. 48 (1980) 669–672.

Further, a focusing lens in EP-A1-0 305 109 creates a substantially parallel-sided beam incident upon the detector, or a beam of at least of reduced divergence compared to the fan-shaped spread of light reflected from the sensing surface with the object to reduce stray light reflections in the detector array. The disadvantages of this apparatus, however, are as follows. The approach, to use a small illuminated area in relation to the sensitive layer for sensing, in order to reduce effects due to inevitable variations in a commercially produced metal film and coating of antibody. In fact, the surface concentration of bound sample molecules will in general also be non-uniform across the sensitive layer and strongly dependent on mass transport conditions. Thus, the small sensing area will be very sensitive to local variations of the sensing surface and its sample surface concentration resulting in low accuracy of the SPR response. Due to stray light arising from the coupling optics and a reflection in the sensor surface, it is possible to use the described optical system for monitoring beams from separate sensitive areas simultaneously by its own detector in an array only under the condition that the array can be conveniently placed close to the exit surface of the hemicylinder or attached to or deposited on that surface. This leads to limitations in the resolution of individual sensitive areas on the detector array, expensive optoelectronic constructions, complicated production process (detector alignment, optimization of collected angle span etc.). Optical oil or grease may be used to ensure good optical coupling between the hemisphere and the sensor substrate (glass support plate or slide).

The an approach of a disposable hemicylinder as optional technical solution for the change of sensor surface is unpractical due to the high costs of an adequate optical quality of this component and the critical optical alignment relative to the light source.

With regard to the use of internal reflection procedures, most of the present publications laboratory equipment for a singular determination of a specific substance at a time. Such equipments, however, are not suitable as practical commercial instruments; they are too complex and cumbersome in their construction for sample and liquid handling, detection, and evaluation, and the analysis procedures take quite a long time and moreover require highly skilled operators in order to obtain accurate results.

By the present invention a new analytical system is provided for at least one specifically sensing surface comprising the simultaneous detection of a plurality of specific interactions, in that it is adaptable for detection techniques based on cylindrically focused total internal reflection and internal Brewster angle reflectometry.

Thus, in one embodiment of the present invention, means for employing internal multiple-angle Brewster angle reflectometry on an exchangeable sensing surface for a new analytical system by use of a stationary optical system is provided.

By another embodiment of the present invention, means for employing multiple-angle evanescent ellipsometry on an exchangeable sensing surface is provided for a new analytical system by use of a stationary optical system.

In another embodiment of the present invention, a new analytical system is provided enabling variable-angle total internal reflection fluorescence on an exchangeable sensing surface by use of a stationary optical system.

In a still further embodiment of the present invention a new analytical system is provided enabling variable-angle scattered total internal reflectance (STIR) on an exchangeable sensing surface by use of a stationary optical system.

According to a preferred embodiment the present biosensor system uses a new mean-value procedure, utilizing an anamorphic lens system, for the detected reflectrometric, emitted or scattered light due to a specific interaction at a sensing surface that is optimized relative to the flow cell geometry, permitting inherently accurate and highly sensitive results to be obtained.

Furthermore, in a preferred embodiment a the present invention provides a biosensor analytical system that eliminates the drawbacks related with more or less stationary sensing surfaces, generally being coated on expensive prisms or wave guides, by introducing a separate sensor unit that is semi-automatically exchangeable in the instrument. Such a sensor unit having at least two sensing surfaces, as well as a method for its functionalization, is the object of our copending PCT-application entitled "Sensor unit and its use in biosensor systems", now PCT Publication No. WO 90/05305 (based upon Swedish patent application No. 8804074-6), the disclosure of which is incorporated by reference herein.

Moreover, the present biosensor system provides a in a preferred embodiment thereof, an automated integrated liquid handling block, micro-processor controlled valves therein, preferably membrane valves, enabling complex liquid handling tasks comprising specific sequences of addition of various ligands, macromolecules, and reactants for interaction at the sensing unit.

The biosensor system of the present invention enables new applications related to the field of characterizing biomolecules to be performed, e.g. as disclosed in our copending PCT-application entitled "A method of characterizing macromolecules" now PCT Publication No. WO 90/05306 (based upon Swedish patent application No. 8902043-2), the disclosure of which is incorporated by reference herein; as well as in our aforesaid copending PCT-application entitled "Sensor unit and its use in biosensor systems". Such new applications made possible by the present invention comprise:

qualitative as well as quantitative specific determination of at least one biomolecule in a sample either simultaneously or sequentially, qualitative as well as quantitative structural information of macromolecules through the detection of interactions between surface-exposed structural elements on the macromolecule and various ligands, functional/structural information of macromolecules, kinetic information about molecular interactions, specific functionalization of at least one sensing surface on the sensor unit, regeneration or changing of the specific functionalization of at least one sensing surface on the sensor unit.

In accordance with the above, the optical biosensor system of this invention comprises at least one, but preferably a number of sensing surfaces or areas arranged in side-by-side relationship for being exposed to sample liquid passing over them. These sensing surfaces are analyzed by the above-mentioned optical techniques based on a single source of light so that due to the use of one identical set of wavelengths for all the sensing surfaces it is now possible to obtain a calibration, reference and evaluation process of such high analytical performance that this biosensor system becomes commercially useful. The system is also such that the sample liquid can be made to sweep over the sensing surfaces all at the same time or in a sequence. Measurements are made under controlled temperature conditions. At the time when the measurement is being performed the temperature at all the sensing surfaces is to be the same and is to be kept constant during the measuring operation.

The sensing surface or surfaces of the sensor unit will lend themselves readily and simply to functionalization individually, for selective interaction with the desired biomolecules; that is, it will be easy to bestow different affinity properties on these sensing surfaces.

The provision, in accordance with the above mentioned preferred embodiment, of a block unit for liquid handling using automated microprocessor-controlled sample insertion and sample guiding valves will permit precise and reproducible dispersion of the sample zone and accurately determined amounts and flow rates of sample solutions, reagent solutions or reference solutions.

The advantages of an integrated conduit liquid handling system situated in a permanent rigid and planar structure has been described by Ruzicka (Ruzicka, J., Analytical Chemistry, 55, 1041A (1983)). Hence, the rigidity of such a structure and the possibility to integrate and control sample injection ensures repeatability of dispersion of the sample zone. Further, the small dimensions of the microconduits reduces sample reagent consumption to the microliter level. Furthermore, the versatile combination of engraved grooves as conduits within laminated parallel layers, interconnected by perpendicular channels, provides the means for integrating a number of highly controlled solution handling tasks. The technical limit on possible miniaturisation of such flow injection analysis systems has, however, been the availability of detectors suitable for sub-microliter detector volumes. The present invention comprises in one particular embodiment thereof a multi-analytical system enabling a detector volume of and below 60 nanoliter.

Thus the liquid handling block unit of the present biosensor system contains conduits or channels having one or more portions which, when the measuring operation is to be performed, are pressed against the sensor unit to thus form one or more flow cells, the arrangement being such that these flow cells can either be coupled in series or be made to each receive its own sample solution separately. A flow cell may contain a single sensing surface or alternatively a plurality of sensing surfaces; in this latter case, the sensing surfaces lie in a row in the longitudinal flow direction of the flow cell. The block unit for liquid handling is to be employed both when the sensing surfaces on the sensor unit are being functionalized and when analysis is carried out.

Furthermore, the optical biosensor system according to this invention provides for a stationary optical instrumentation, without any movable parts. Thereby the optical system may already in the course of its manufacture in the factory be given a fixed, "once for all" standard setting so that this setting does not need to be altered during the subsequent use of the system. In view of this fixed setting it is possible to have the optical system mounted inside a dust- and light-tight housing. Moreover no smeary oils need to be employed for coupling the light to the replaceable sensor unit. Instead a replaceable opto-interface may be used for coupling light from the light source to the sensor unit. Such an opto-interface is disclosed in our copending PCT-application entitled "Optical interface means", the disclosure of which is incorporated by reference herein.

As mentioned above the measurement accuracy may be still further increased by establishing an optical and, respectively, electronic mean value procedure as will be described in detail below; this is so because the establishment of such mean values will permit an accurate determination of the quantitative or relative amount of specific biomolecules that have adhered to the individual sensing surfaces.

With the features mentioned above, an optical biosensor-based analytical system is obtained that permits fast automated high-precision measurements of extremely low concentrations, nanomolar and even down to picomolar, and with a high response dynamics. In, for example, the SPR biosensor system the resonance angle may be measured over a wide range of angles.

The invention will now be described in greater detail below, with reference to the attached drawings in which FIG. 1 is a schematic exploded view of an optical biosensor system according to the present invention, FIG. 1A is a partial cross-sectional view of FIG. 1 showing a valve in its open position, and FIG. 1B is a corresponding view showing the valve in its closed condition, FIG. 1C is an illustration of an electromagnetic valve in its closed condition.

Figure 1:
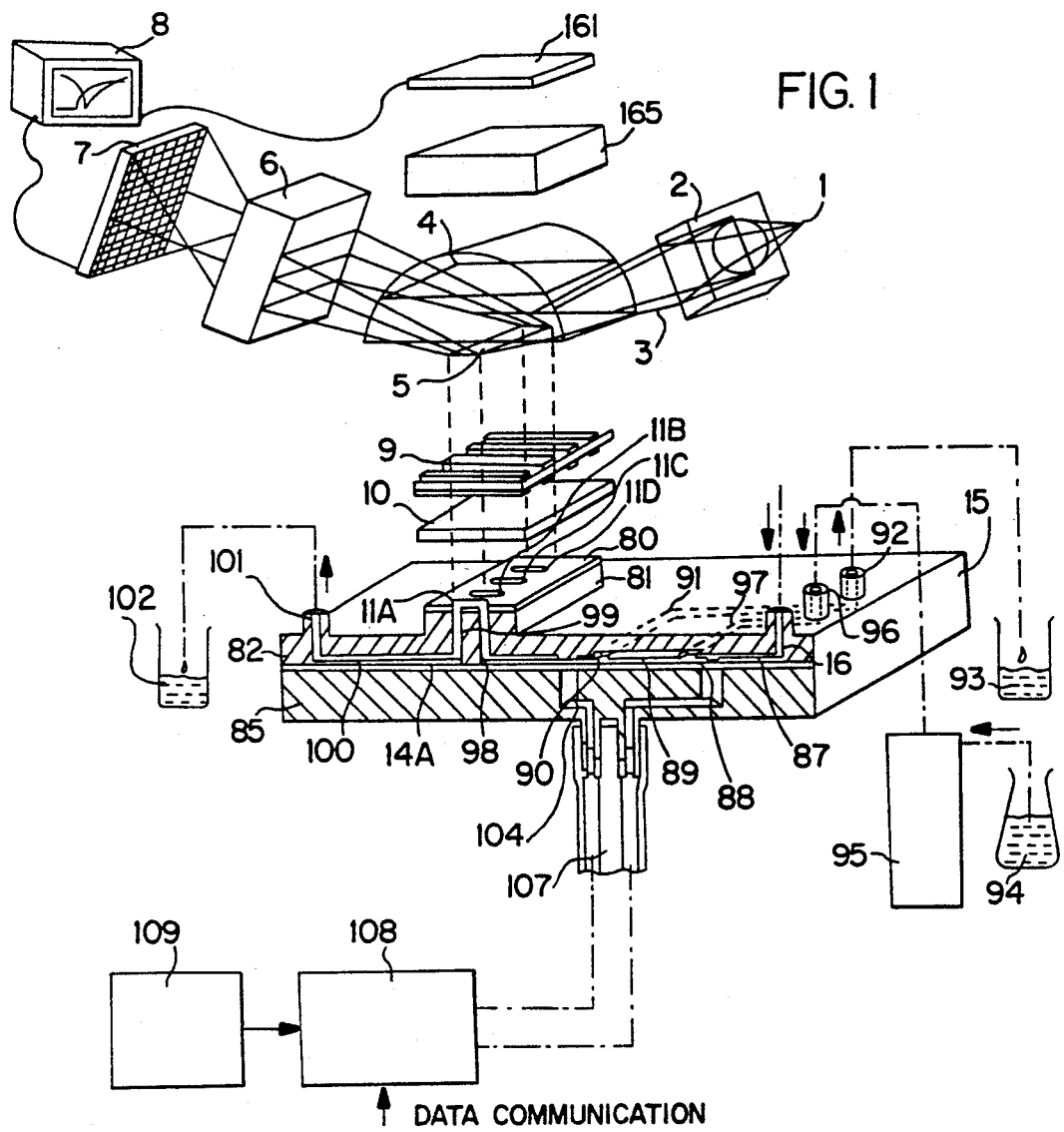
Figure 12:
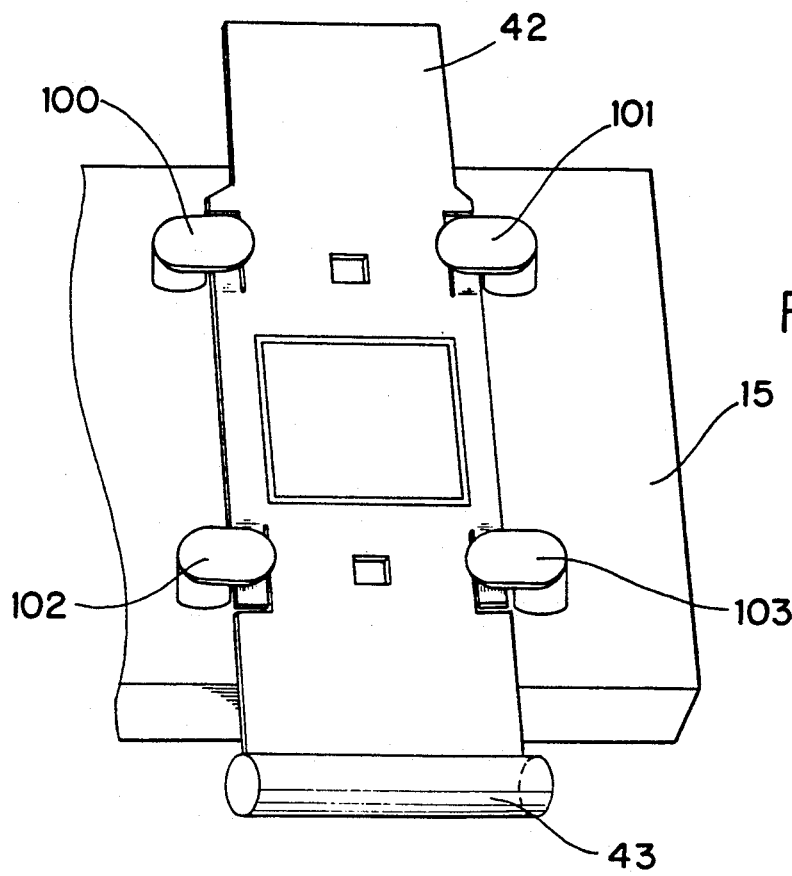
Figure 7:
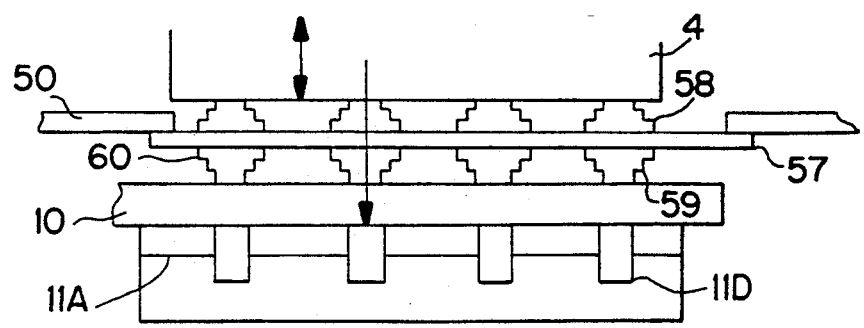
Figure 8:
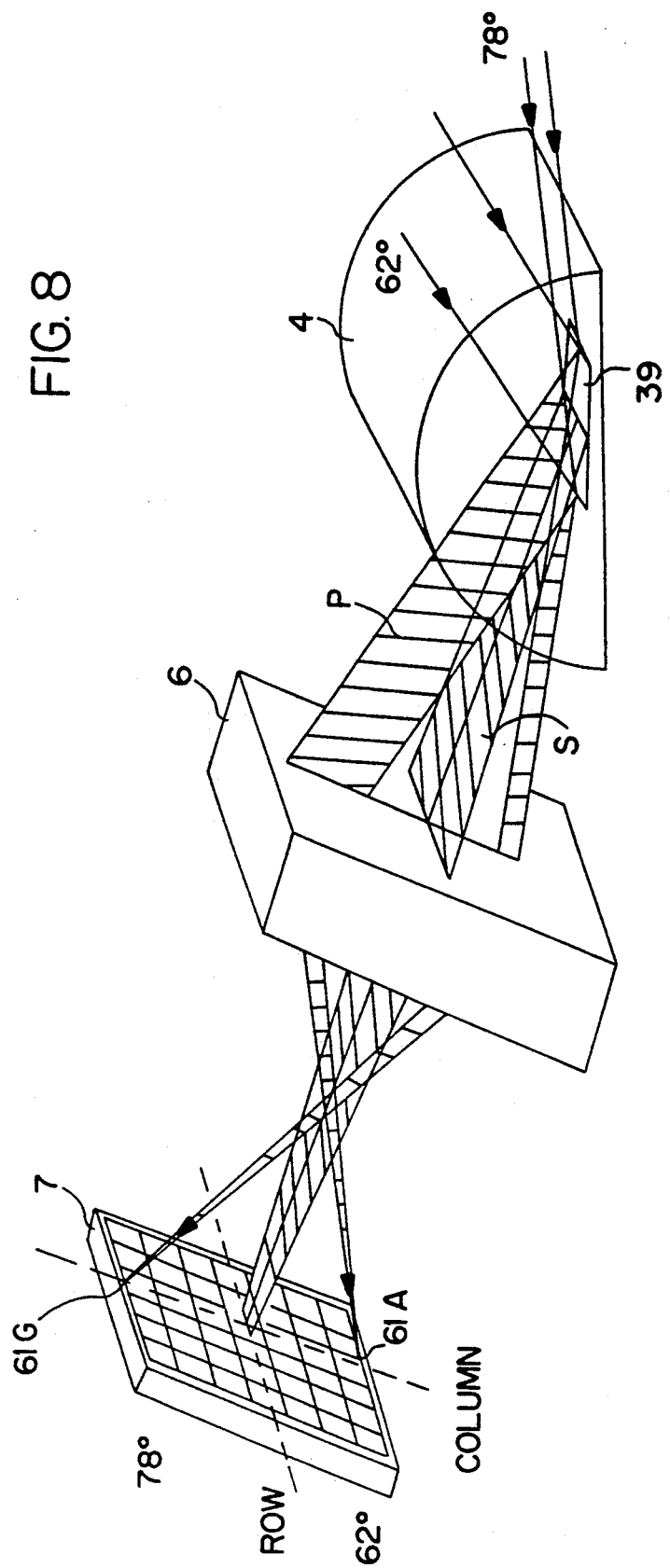
Figure 9:
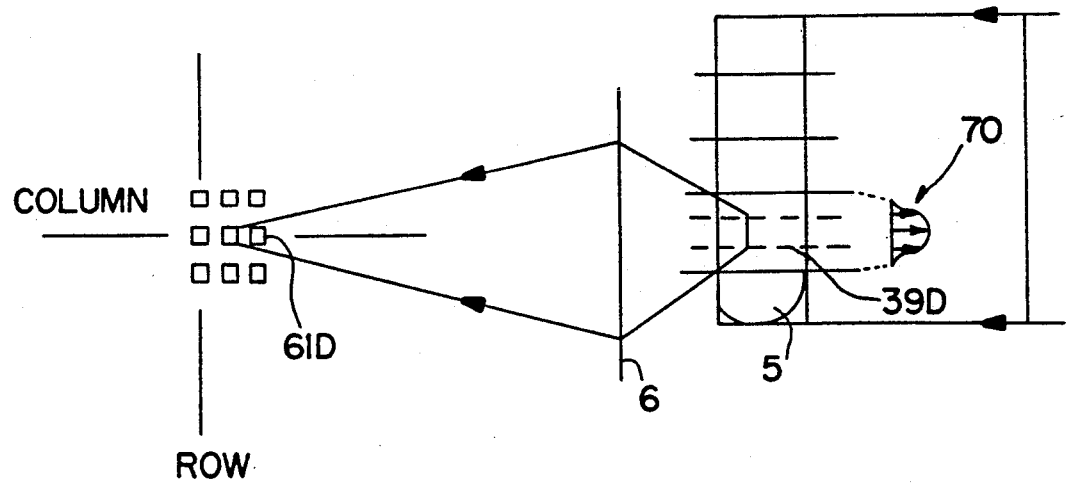
Figure 10:
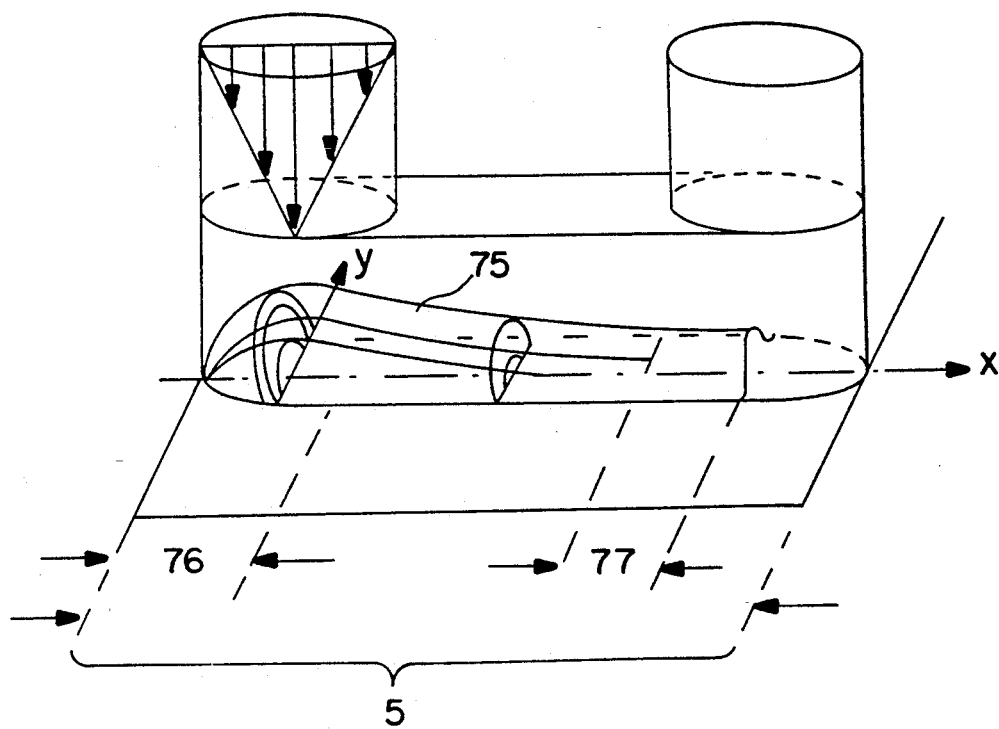
Figure 11:
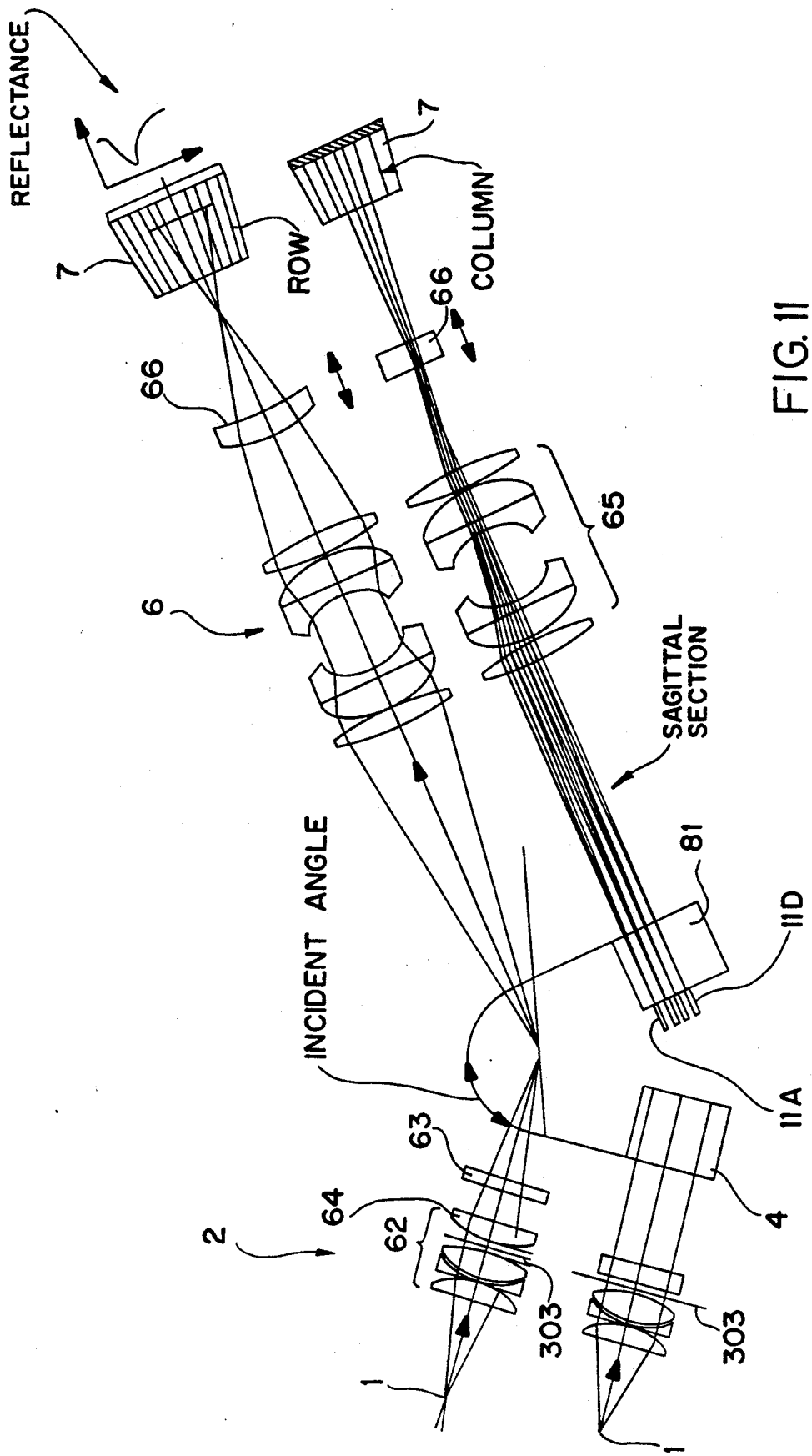
Figure 13:
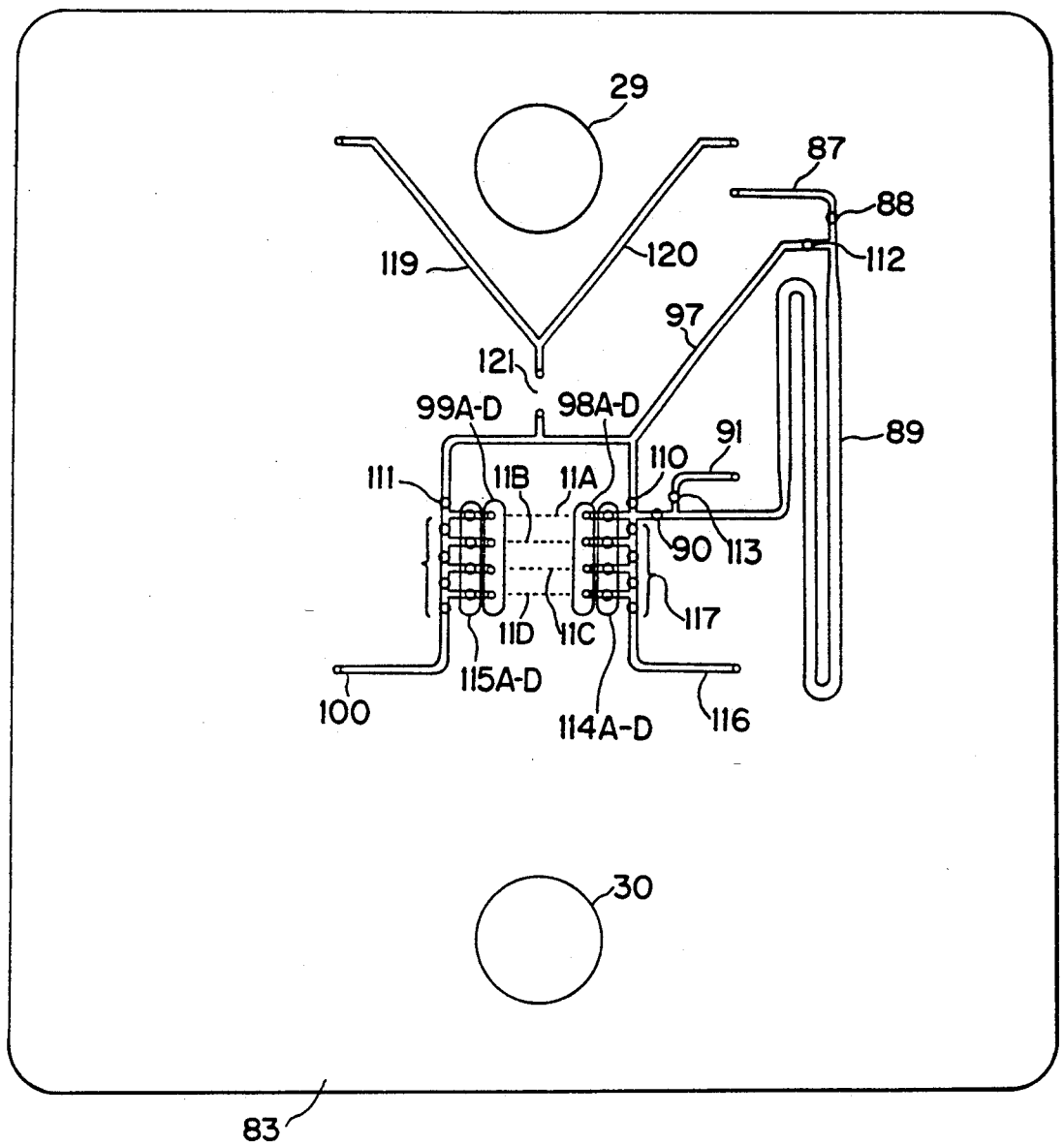
Figure 14A:
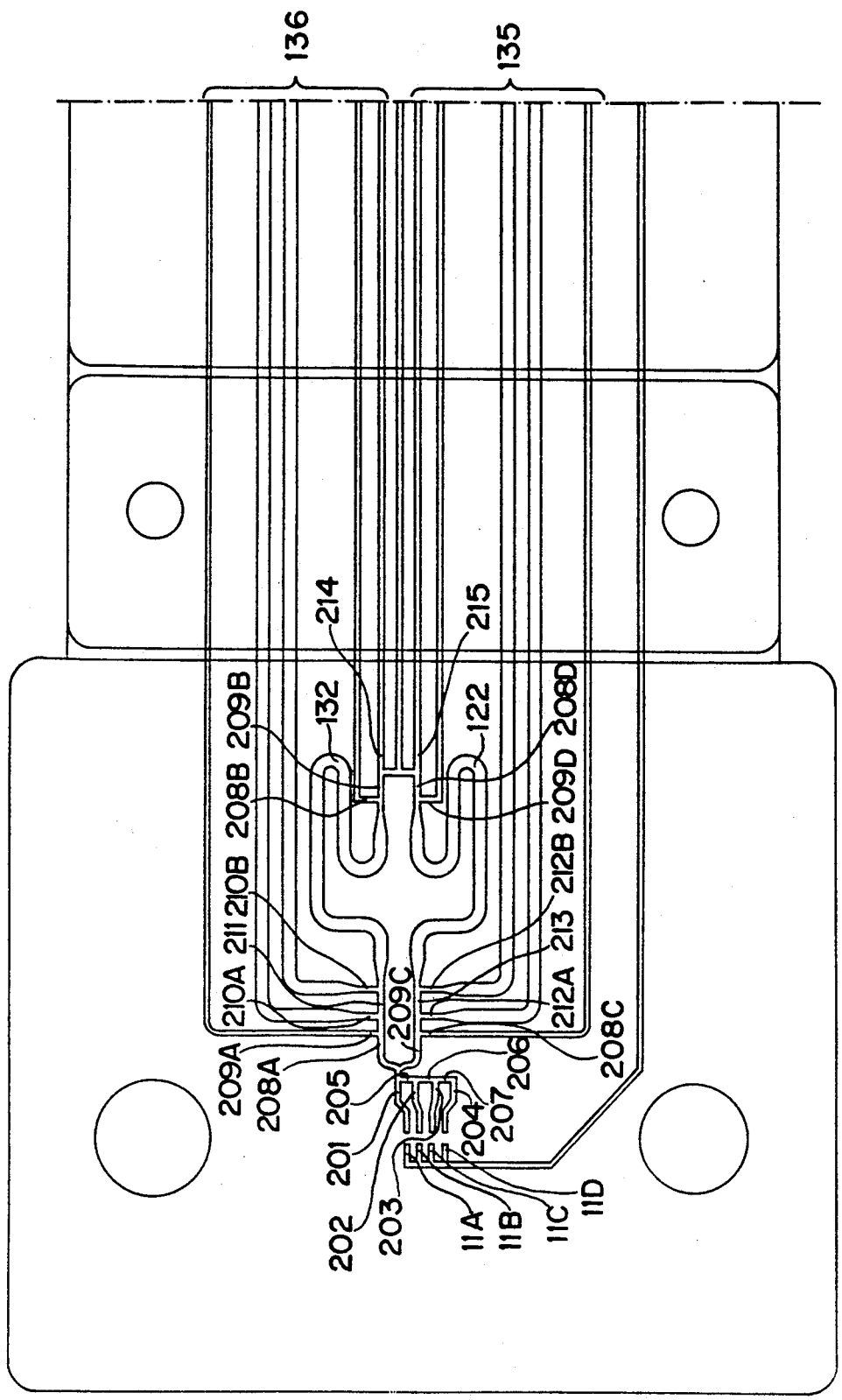
Figure 14B:
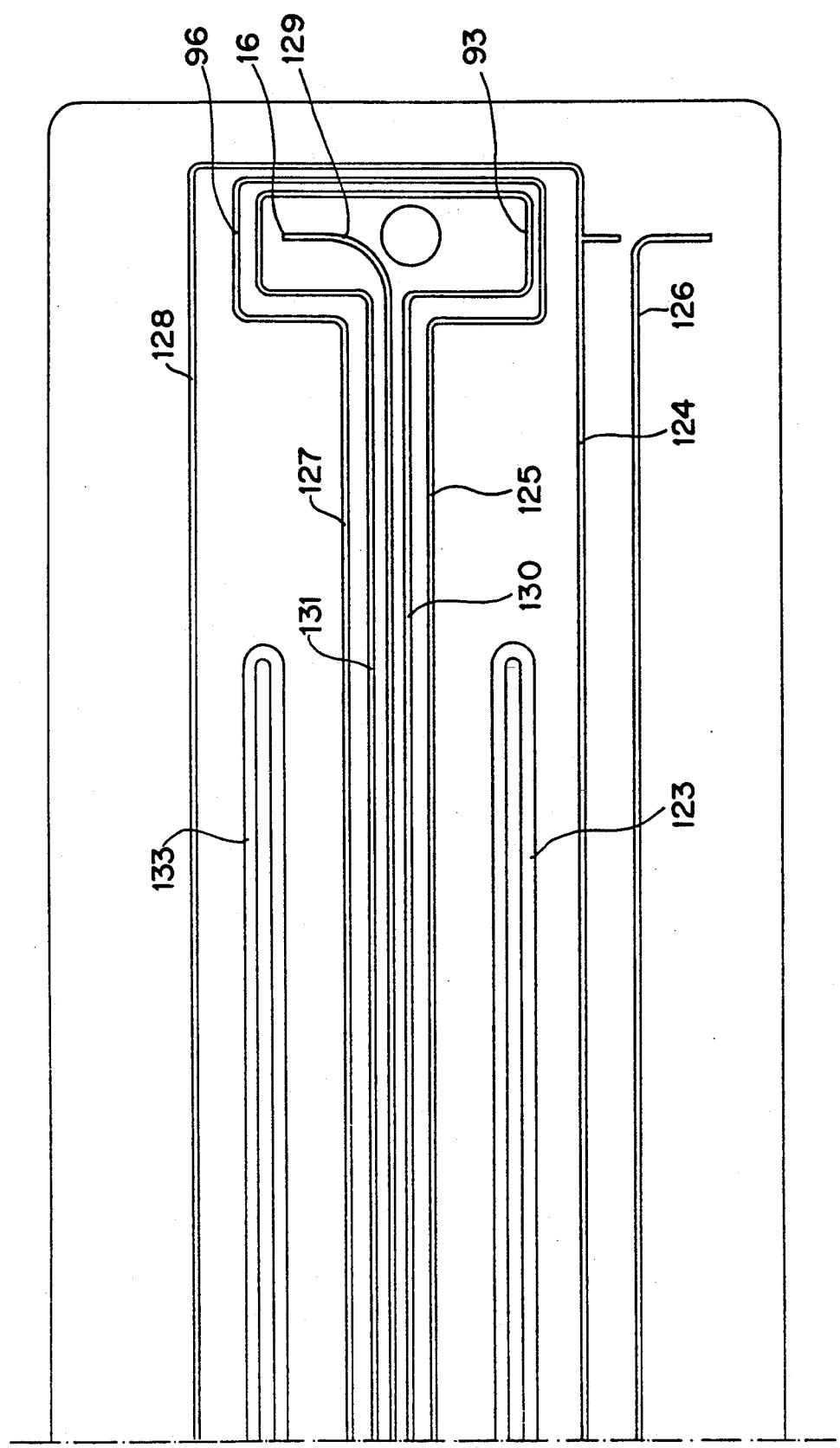
Figure 15:
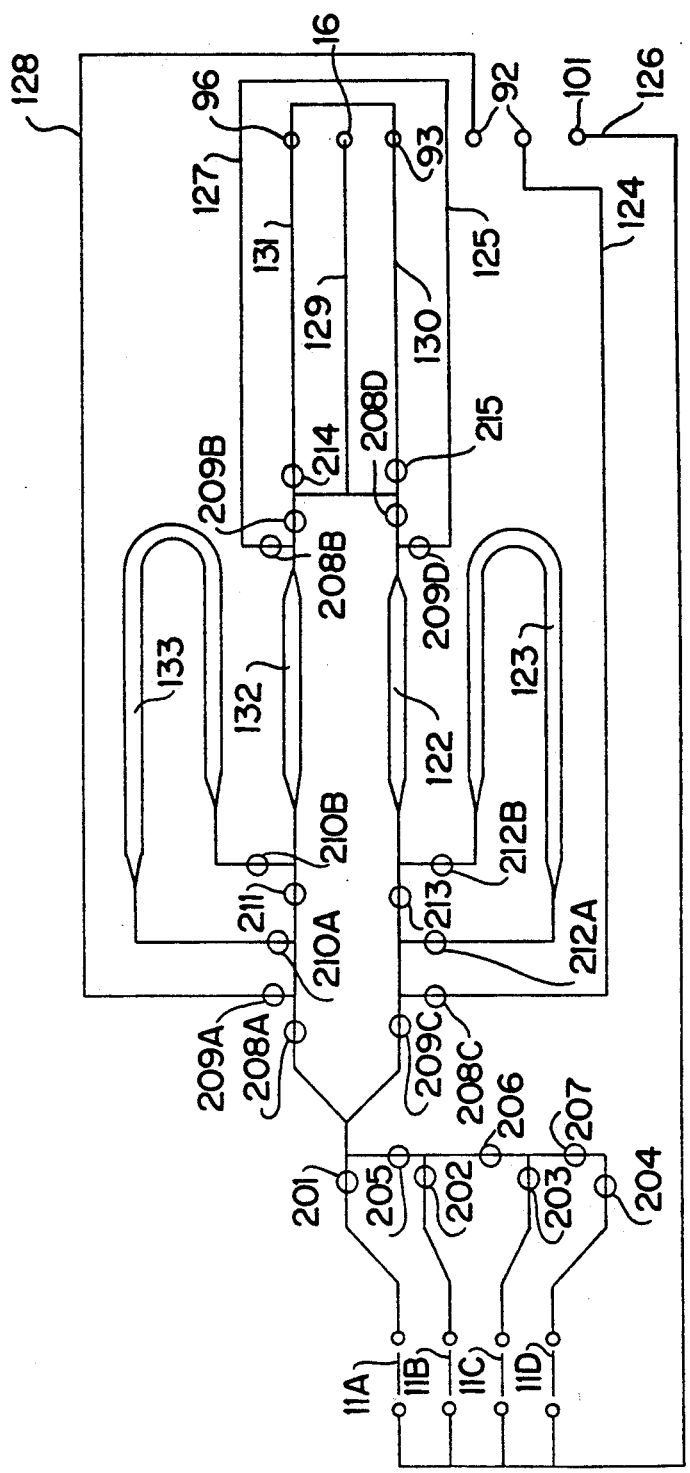
Figure 16:
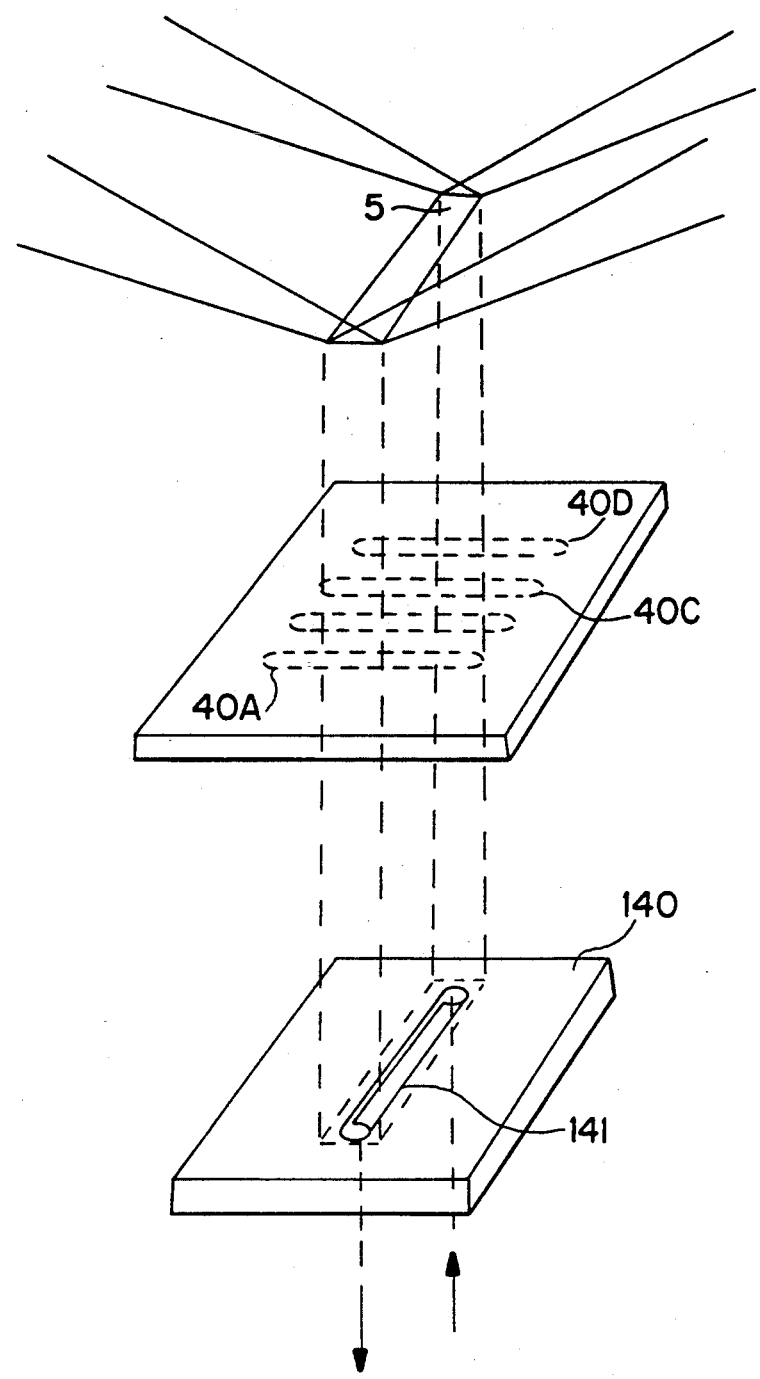

FIG. 7 is a sectional view of the opto-interface mechanically coupled to the sensor unit, FIG. 8 is a schematic perspective view of the refractive characteristics of the anamorphic lens system, showing the creation of an optical mean value of the mass of biomolecules bound to the sensing surface, as seen along the width of the streak of light, this being achieved in that light rays in the plane P reflected at a certain specific angle irrespective of the point of reflection on the sensitized surface are imaged on a row of detector elements, and how in the plane S light rays from an individual sensing surface are imaged on a column of detector elements, FIG. 9 is a schematic plan view in the S plane of the incident collimated beam of light, showing the creation of an electronic mean value of the mass of biomolecules bound to the sensing surface, as seen in the longitudinal direction of the beam of light, FIG. 10 is a schematic perspective view of the flow cell, illustrating the flow conditions therein and the creation of an integrated optical mean value of the mass of bound biomolecules, FIG. 11 shows a meridian section of the light source, a coupling prism and the anamorphic imaging system, and the first and second lens means; and a sagittal view of the same items, FIG. 12 is a perspective view of a carrier and sensor unit in relation to a block unit for liquid handling, FIG. 13 shows a plan view of the underside of the base plate in the FIG. 1 block unit for liquid handling, FIGS. 14A and 14B taken together show a plan view of the base plate according to another embodiment of a block unit for liquid handling, FIG. 15 schematically shows the functions of the block unit for liquid handling according to FIGS. 14A and 14B, and FIG. 16 shows another embodiment of a flow cell in longitudinal or parallel mode in relation to light streak 5.

FIG. 1 shows the main components of the optical biosensor system according to this invention, in the form of an exploded view. The system comprises a source of light 1, first lens means 2 for directing a transversely extending convergent beam 3 toward a prism 4 whereby the beam is focused in the bottom surface of the prism to thus form a streak 5 of light. Rays of light reflected from the sensitized surfaces are imaged via an anamorphic lens system 6 on a two-dimensional photodetector device 7. The electric signals created by the photodetectors are processed in an evaluation device 8 in the form of a computer. By means of the prism and an opto-interface 9 light from streak 5 is directed to a sensor unit 10 which is to lie in contact with a number of parallel, upwardly open portions 11A–D of flow channels 14A to 14D respectively; only one of these, 14A, is shown. The flow channels form part of a block unit 15 for liquid handling, this unit being provided with schematically indicated inlet connection means 16 and 96 and outlet connection means 101 and 92.

Figure 2:
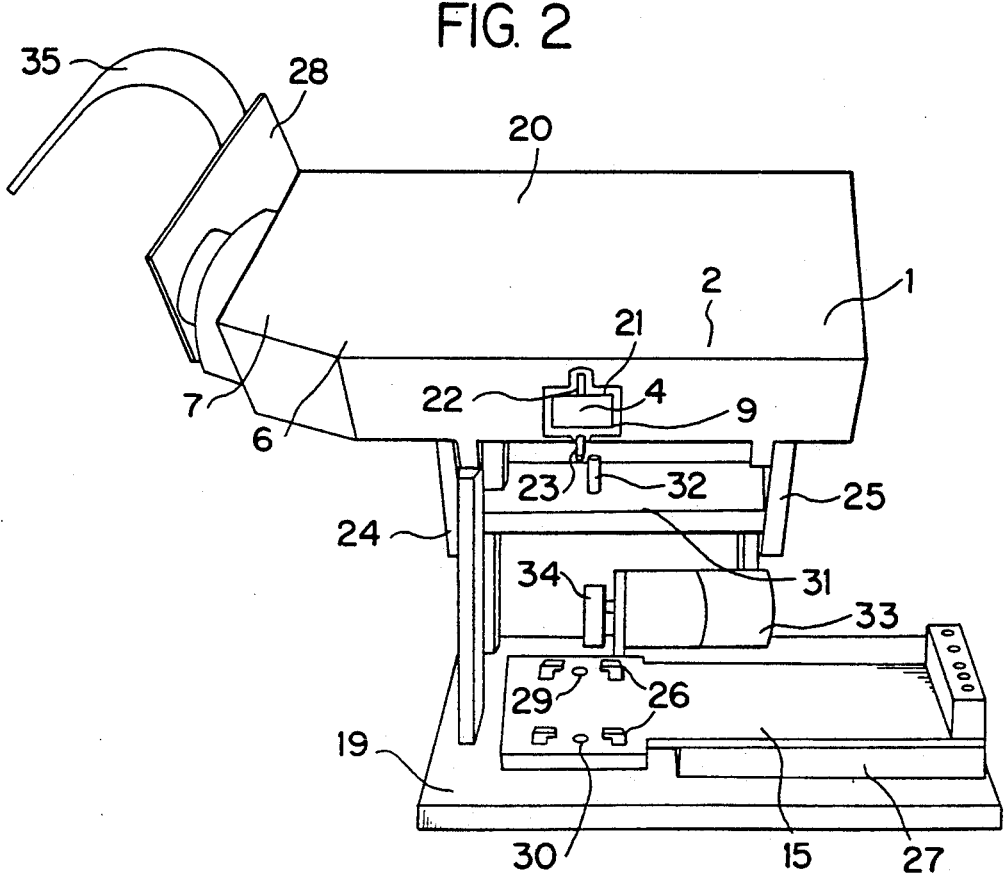
FIG. 2 is a perspective view of the central part of the biosensor system.

FIG. 2 is a perspective view of the analytical apparatus, generally designated 18, which is the heart of the optical sensor system according to the invention. The apparatus comprises a support 19 on which the block unit 15 for liquid handling is mounted in a fixed position, and furthermore comprises a housing 20 in which the light source 1, the first lens means 2, the prism 4, the imaging optical unit 6 and the photodetector device 7 are accommodated in fixed positions. An aperture 21 in the bottom portion of the housing is to be covered by the opto-interface 9 which is retained in its desired position by means of two guide pins 22, 23. The housing 20 is hinged to the support by means of a system of articulated arms 24, 25 pivotally attached to the housing and to the support respectively. The block unit 15 for liquid handling carries a number of holder means 26 for the sensor unit in its carrier plate. As shown in detail in FIG. 12 the holder means are L-shaped angle pieces on top of the upper face of the block unit for liquid handling, thus forming guide means enabling the sensor unit to be slid over said block unit. A thermostat means, not shown in FIG. 2, surrounds prism 4. This thermostat means consists of channels for liquid in a heat exchanger block which maintains the metal frame around aperture 21 at a constant temperature. A similar thermostat means 27 placed between the block unit for liquid handling and the support is to maintain the liquids in the channeling system of said block unit at the same constant temperature as that stated above. The photodetector device is accommodated on a printed circuit card 28 mounted in a fixed position at one of the end faces of the housing 20. Guide pins 22, 23 are received in openings 29, 30 provided in the block unit for liquid handling. A transverse beam member 31 extending between the arms 24, 25 carries a projecting peg 32 for rotating the housing 20 back and forth between two positions, viz., an analysis position and a loading position. These will be described later in greater detail. An electric motor 33 which is attached to the support has an output shaft carrying a disk 34 excentrically, and the peg 32 is in contact with the periphery of that disk 34. By activation of the electric motor so that the excentrically mounted disk 34 rotates through a predetermined angle the housing is automatically swung into and out of these analysis and loading positions without any manual operation. A flat cable 35, shown schematically, goes from the printed circuit card 28 to the evaluation device 8.

Figure 3:
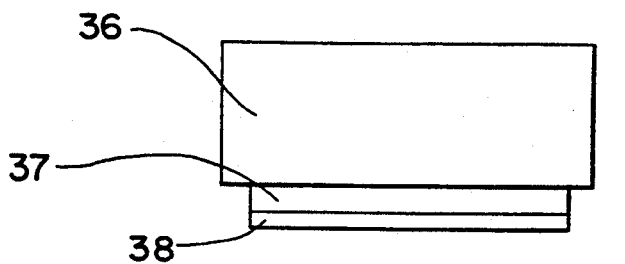
FIG. 3 is a cross-sectional view of a sensor unit.

FIG. 3 shows the sensor unit 10 in cross section. In our copending Swedish patent application entitled "Sensor unit and its use in biosensor systems" this sensor unit is described in greater detail. The sensor unit comprises a transparent plate 36 of glass, plastics or other transparent material. On one of its faces the plate is provided with a metal film 37 that has been applied by e.g. sputtering. A dielectric film 38 is attached to the metal film. In the preferred embodiment of the invention, the dielectric film is a layer of dextran bound to the metal film. By means of a coupling technique such as is known in biotechnology, ligands are bound to the dextran film which serve to interact with specific biomolecules present in the sample solution. For attaching the ligands the sensor unit with its metal film and the dextran layer thereon is contacted sealingly with the upwardly open portions 11A-D of all the flow channels 14A-D. By pumping a solution containing a specific ligand L1 into one of the channels, 14A, another specific ligand L2 into the second channel, 14B, a third specific ligand L3 into the third channel, 14C etc., a corresponding number of sensing surfaces may be produced on a single metal film with each its own individual affinity for a (respective) specific biomolecule. The ligands may for example be bifunctional or polyfunctional molecules having one active portion consisting of antidextran and another portion consisting of an antigen to the antibody that is to be detected. As a result of this functionalization, the optical biosensor system of the invention may be tailored individually by the user so as to be rendered useful for detection of just those biomolecules in which he is interested. This functionalization will permit inter alia qualitative analyses. The functionalized sensor unit is introduced into the analytical apparatus or functionalized in situ, whereupon the analysis is carried out. When the analysis operation has been finished the sensor unit is regenerated in that the sensing surfaces are "washed" with a solution that will disrupt the coupling between the ligands and the dextran film 38.

Figure 4:
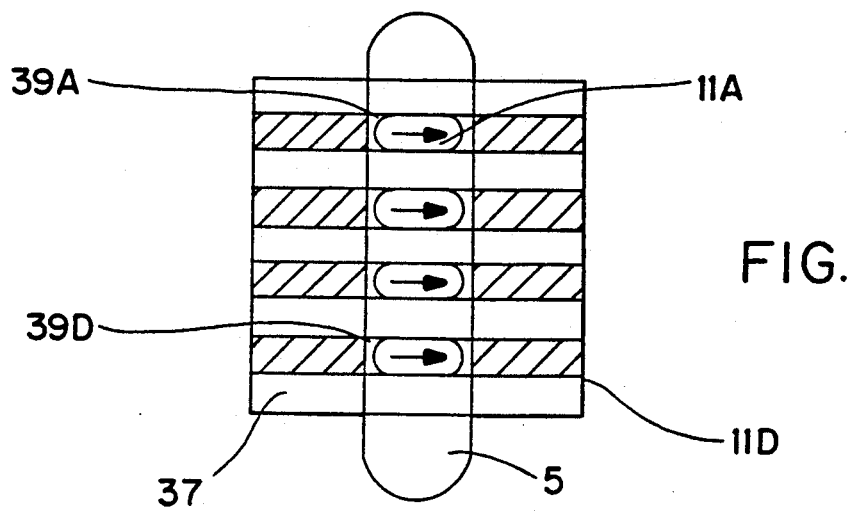
FIG. 4 is a top view of an irradiated sensor unit.

FIG. 4 is a top view of the sensor unit 10 of FIG. 3. The sensor unit has been placed on top of the upwardly open portions 11A-D, and the streak 5 of light arriving from lens system 2 of light source 1 irradiates the reverse side of metal film 37. As will be seen from the above description regarding the activation of dextran film 38, sensing surfaces 39A-D are formed each corresponding to the length of the open portions 11A-D (provided the sensor unit is attached to the liquid handling block unit with the same orientation both in the analysis phase and in the sensitation phase). Light streak 5 extends transversely over the sensing surfaces 39A-D and has a width at least equal to the length of portions 11A-D.

Figure 5:
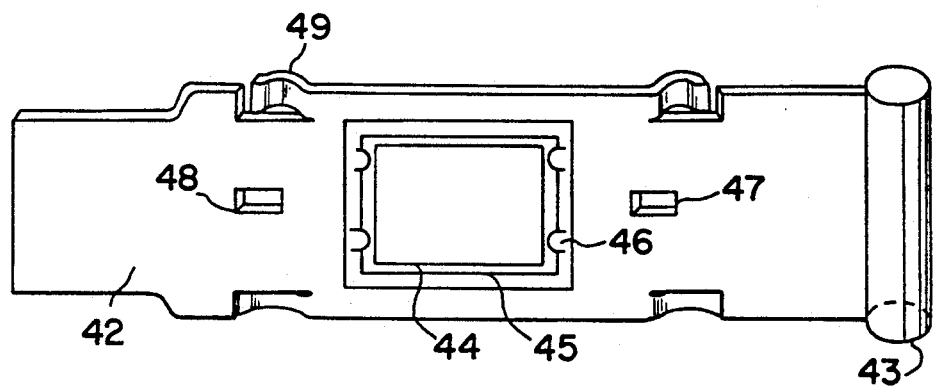
FIG. 5 is a perspective view of a carrier plate for the sensor unit.

In FIG. 4, the metal surface 37 is presented on a magnified scale. In actual practice the metal surface will be a square of say an order of magnitude of about 10×10 mm, the dimensions of the transparent plate then being somewhat larger, e.g. 11×11 mm. Such a construct is difficult to handle without tweezers or other seizing means. But such procedures involving the use of seizing tools are undesirable because they tend to thwart high-precision measurement. What is proposed instead, according to the present invention, is that each sensor unit is mounted on a carrier plate which can easily be seized between forefinger and thumb. A plan view of the carrier plate is shown in FIG. 5; the plate comprises an elongated sheet of plastic 42 with a grip area 43. An opening 44 through the carrier plate has a flange 45 on which the sensor unit will be resting. Clasps 46 projecting laterally from the flange surface serve to retain the sensor unit between the flange and clasps. The sheet 42 has two guide holes 47, 48 through which the guide pins 22, 23 will pass in the analysis position of the apparatus. When the apparatus is in its loading position the guide pins are retracted both from said guide holes 47, 48 and from the openings 29, 30, the carrier plate being now free to be slid into its position on the block unit for liquid handling or, respectively, to be drawn off therefrom.

Sheet 42 also has control springs 49 for (i) facilitating introduction of the sensor unit into the liquid handling block unit and (ii) protecting the sensor unit from damage or e.g. scratches in case the carrier plate is unintentionally set down on a table or the like. It is preferable to accommodate the carrier plate and its sensor unit in a housing which comprises top and bottom walls, two side walls and one end wall. The interior faces of the top and bottom walls are provided with pairs of opposite ledges extending longitudinally of the housing. They serve to maintain a clearance space between the carrier plate and the top and bottom walls.

Figure 6:
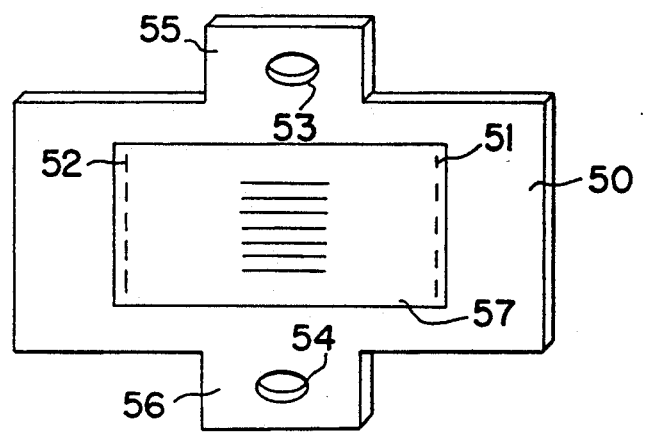
FIG. 6 is a plan view of an opto-interface.

FIG. 6 shows a plan view of an opto-interface plate according to the present invention. The plate is fastened on a metal frame which has two projecting tongues 55, 56, said tongues being provided with one hole each, these holes 53, 54 extending all through the thickness of the tongues and serving to receive the guide pins 22, 23. The frame has two flanges 51, 52 against which a transparent plate 57 of glass or plastic has been applied. As shown in FIG. 7, on one face plate 57 is provided a number of longitudinally extending parallel ridges 58 in side-by-side relationship. On its opposite face the plate has a corresponding number of parallel longitudinal ridges 59 lying opposite the ridges of the first-named plate face. The ridges are made of a transparent elastic material and spaced apart a distance corresponding to that between the upwardly open portions 11A-D of the flow channels. As seen more clearly from FIG. 7 the ridges 58, 59 have longitudinally extending stepped portions 60 at each side to thus form a structure having in cross section the configuration of a flight of stairs, the uppermost step or top platform of each of these stepped structures being capable of being pressed resiliently against the transparent plate 36 of the sensor unit and, respectively, the prism 4. This stepped configuration prevents air pockets from being formed between the interfaces contiguous to the prism and, respectively, plate 36 of the sensor unit. FIG. 7 shows the prism 4, the opto-interface plate and the sensor unit in the analysis position of the analytical apparatus 18. Ridges 58, 59 are spaced apart in such a manner that the distances between them correspond to the distances between the upwardly open portions 11A-D of the flow channels 14A-D.

This arrangement of the ridges 58, 59 on the opto-interface plate, the holes 53, 54 for the guide pins 22, 23, the holes 47, 48 on the carrier plate 42 of the sensor unit and the stationary mounting of the upwardly open portions 11A-D of the block unit for liquid handling ensure that the lower ridges 59 will serve as sources of light which lie directly above each of the corresponding channel portions 11A-D. No scattered light from neighboring ridges 59 will interfere with the resonance angle determination for the individual sensing surfaces. In this manner it is possible to have a great number of these channel portions packed next to one another. As an example, it may be mentioned that up to 20 of such upwardly open channel portions can be packed together within a breadth of about 10 mm without any scattered light interfering with the measuring operation.

FIGS. 8-11 illustrate the optical system in the analytic apparatus according to the invention. The basic principle of the anamorphic lens system 6 is shown in FIG. 8. The broad beam of light which is wedge-shaped or convergent strikes the illustrated sensitized surface, e.g. at sensing surface 39, at angles of incidence of from 62 to 78 degrees. Rays with all the intermediate (between 62° and 78°) angles of incidence are present in the beam. Consider only one incident plane P. All the rays incident with for example an angle of 62° are indicated by white arrows, are reflected on the sensitized surface and will be imaged on only one single photodetector 61A by the anamorphic lens system. Similarly, all the rays incident with an angle of 78° and indicated by black arrows will be imaged by the anamorphic lens system on one single photodetector 61G of the photodetector device 7. Light rays having incident angle values intermediate between 62 and 78 degrees will similarly strike those photodetectors which are situated between detectors 61A and 61G in the same photodetector column; in FIG. 8 this is illustrated as being a vertical column.

Light source 1, e.g. a light emitting diode, emits a type of light that is substantially monochromatic in character ($\pm 30$ nm), and furthermore is incoherent and has a center wavelength of an order of magnitude of about 650 to about 850 nm. Alternatively, the light source 1 is a laser, e.g. a semiconductor laser, a dye laser or a gas laser, emitting substantially monochromatic and coherent light. The light passes through the first lens means 2, which in the case that light source 1 is a light emitting diode includes an interference filter 303 for forming a wedge-shaped convergent elongated beam which passes through a plane polarizer 63 indicated schematically in FIG. 11 and then on toward the bottom face of prism 4. In that bottom face and on the underside of metal film 37 a streak of light is formed having a width which is adjustable by means of a cylindrical lens 64. The optical imaging system comprises the anamorphic lens system 6 the function of which has been described above. It contains inter alia a lens 66 for adjusting the degree of magnification of the resonance angle range along photodetector columns.

Light rays having a different plane of incidence parallel to the plane of incidence P will in a similar way be imaged on individual photodetectors belonging to other columns of the two-dimensional photodetector device. Every photodetector of a row thus corresponds to one specific angle of incidence. As against this, conditions are different in the case of the reflected light obtained from light that is reflected in an S plane, i.e. in planes differing from the plane of incidence P of the convergent beam. Such light will image a point on the sensitized surface as a real image element on detector pixel 61D. Thus to each detector column corresponds a respective part of the sensing surface as seen in the transverse direction of the conduit portion. Depending on the width of the channel, the surface dimensions of the individual photodetectors, and the spaces between them, a particular number of photodetector columns may be required for imaging the total width of the channel portion in question. In a preferred embodiment of the invention a reduced scale image of a large portion of the flow cell width is created on one single column of detectors.

Upon this introductory description of the anamorphic lens system will now follow a description of the mass uptake on a sensing surface, e.g. sensing surface 39D (see FIG. 9). The rate of flow is zero at the side walls of the channel, and then increases toward the center of the channel. The flow profile is shown schematically at 70 where arrow lengths correspond to the flow rates occurring. The channel width is assumed to be about 300 $\mu$m. In order to avoid measuring results becoming distorted by the outer channel regions where no sample liquid is flowing the anamorphic lens system is arranged so as to produce an image of only a narrow portion, say of an order of magnitude of 50% or more of the width of the sensing surface, on a single column of photodetectors; e.g. a 150 $\mu$m central portion of a sensitized surface whose total width is 300 $\mu$m is imaged on a column pixel 61D having a width of 90 $\mu$m. This will electronically produce a mean value of the mass uptake within this central part of the sensing surface. Without such a creation of a mean value of the amount of bound biomolecule as seen in the transverse direction of the channel it would not be possible to obtain such a high degree of reproducibility of the response curve of any given sample concentration of the biomolecule as is required in a commercial-type analytical instrument—except perhaps by putting unrealistically high demands on high reproducibility and control of (i) flow profile in the sample liquid (thickness variation of diffusion layer transversely of the channel), (ii) analysis position of the instrument for optical units 2, 6 relatively to the position of the flow channel, (iii) homogeneousness in respect of ligand density and in respect of ligand accessibility within the dielectric film on the sensing surfaces.

FIG. 10 illustrates the flow conditions prevailing in the channel portion below the sensing surface. The flow rate profile of the sample liquid is illustrated by means of arrows of different lengths. In the 90° bending region of the flow channel a large amount of biomolecules may bind to the sensing surface. Reference numeral 75 designates the distribution of the amount of bound biomolecule. The amount thus bound decreases downstream of the inlet. It will be appreciated that if the resonance angle were to be determined on the basis of only one section, indicated by arrows 76, this would result in one particular value being obtained, while if the resonance angle were determined on the basis of the section indicated by arrows 77 this would result in another value therefor being obtained. In order to make sure that a reliable mean value of the resonance angle is obtained the width of light streak 5 is made to agree, according to the invention, with the length of the upwardly open channel portion. In this manner all the contributions from the amount of bound biomolecule will be included when the mean value of the resonance angle is being determined. An optically created mean value is thus obtained, as seen in the direction transversely of the path of the light beam.

Without creation of a mean value of the amount of bound biomolecule as seen in the longitudinal direction of the channel it would not be possible to obtain reproducibility of the response curve of any given sample concentration of the biomolecule, within a concentration range of interest for analysis purposes, as is required in a commercial-type analytical instrument—except perhaps by putting unrealistically high demands on high reproducibility and control of (i) flow profile in the sample liquid in the longitudinal direction of the channel (thickness variation of diffusion layer in the direction of flow), (ii) sample dispersion in the direction of flow, (iii) homogeneousness with respect to ligand density and with respect to ligand accessibility within the dielectric film on the sensing surface, and (iv) the position of the focused light streak along the channel. With the creation of these mean values, it is possible to eliminate such deterioration of reproducibility as will otherwise occur due to variations in the position of the streak of light caused by variation in the thickness of the sensor plate. Maximum analytical sensitivity in the curve of response vs. concentration, and a minimum sample concentration for the detection, are obtained for a light streak width and thus mean value creation covering the sensing surface at the riser duct that opens out into the flow cell, but with a reduced detectable maximum sample concentration.

The width of light streak 5 is adjustable by means of a cylindrical lens 64 which is shown in FIG. 11. Alternatively, light source 1 and lens means 2 are moved mutually fixed along the optical axis. FIG. 11 illustrates the anamorphic optical system in the form of both a meridian section, uppermost part of the Figure, and a sagittal section, lowermost part of the Figure.

The block unit for liquid handling will now be described.

FIG. 1 shows a flow channel 14A belonging to the upwardly open portion 11A. The flow channels 14B-D belonging to the respective upwardly open portions 11B-D have not been shown here, for the sake of clarity. A first layer 80 of sealing elastomer material, e.g. silicone rubber, has a number of cuts or slits extending therethrough, corresponding to the upwardly open portions 11A-D. The layer has been cast onto a plateau 81 which is integral with a base plate 82. This plate is preferably a solid member made of e.g. plastic, metal, ceramics, silicon. A second layer 83 (FIG. 1A) of elastomer material, for example silicone rubber, has been applied by e.g. casting to the underside of base plate 82. This layer 83 is provided with a system of flow channels formed by casting. A third layer 84, preferably of the same material as layer 83, has been cast onto a support plate 85 of solid material, preferably the same as that of base plate 82.

It will now be understood that when in the analysis position of the analytical apparatus the sensor unit 10 is pressed against layer 80 by the opto-interface 9 the upwardly open portions 11A-D in layer 80 will be sealed in liquid-tight relationship against the sensor unit 10 and form four flow cells. For the sake of simplicity, these flow cells too are designated 11A-D.

There now follows a description of the principle according to which a liquid sample is made to pass through flow cell 11A: By means of a pump (not shown) sample liquid is pumped to inlet tube 16, passes through an inlet channel 87 past an open valve 88 and then goes on through a primary channel 89 having a fixed and well-defined volume, until it reaches a closed valve 90 whence it is directed into a waste channel 91 communicating via a connecting tube 92 with waste disposal means 93.

Next, a valve (not shown) at the upstream end of waste channel 91 is closed. At the same time valve 88 is closed. Sample liquid in the primary volume is now ready to be pumped into the flow cell 11A. This is done with the aid of an eluent solution 94 which is pumped by a pump 95 through an inlet tube 96 to an eluent conduit 97 ending in a valve (not shown in FIG. 1, for the sake of clarity) which is now opened, together with valve 90. Continued pumping of the eluent solution will result in that the advancing eluent solution will press forward against the primary volume of the sample liquid and force it to advance upwardly through a riser duct 98 in the plateau 81, thence into the flow cell 11A, and then down through a riser duct 99 in the plateau and out through an exhaust duct 100 and an outlet tube 101; then from this outlet tube at first the sample solution and then the eluent solution will pass on to a second waste disposal means 102 for sample and eluent solutions. When the sample solution which has a predetermined volume is passing along flow cell 11A the chemical action exerted by the sample solution on the sensor unit is analyzed optically.

Valves 88, 90 and the other valves which have not been shown in the drawing are identical in construction; therefore, only valve 88 will be described. The valve comprises a diaphragm 103 opposite a channel or through opening 104 in the support plate 85. The valve diaphragm is an integral part of layer 84. A valve seat 105 formed in layer 83 is an integral part of that layer and has the shape of a projection 105. The portion of channel 104 leading to the valve is filled with a short liquid column 106 of e.g. glycerol. Via a compressed air supply line 107 and an electromagnetically operated compressed-air valve 108 (shown only schematically) the channel 104 communicates with a source 109 of compressed air. The compressed-air valve 108 acts in response to electric signals from the evaluation device 8 which is here embodied in the form of a computer. FIG. 1A shows the valve 88 in its open position while FIG. 1B shows the same valve in its closed position. Were it not for the liquid column 106 the compressed air would penetrate through 84 and pass into the channel system in the form of undesirable air bubbles.

FIG. 13 shows an embodiment of the channel system in a block unit for liquid handling. Dotted lines 11A-D symbolize the four flow cells each having their riser tube connection. The small circular rings indicate valves each of which has a construction as explained above. Eluent conduit 97 contains valves 110, 111, 112 in the places where shown. Waste duct 91 has a valve 113. Immediately upstream of riser tubes 98A-D there are valves 114A-D, simply designated by the common numeral 114 in FIG. 13, for the sake of clarity. Immediately downstream of riser tubes 99A-D there are valves 115A-D; here again the valves are symbolized by only one common numeral, 115. A second waste duct, designated 116, has valves 117A-D in the places where shown; their one common numeral is 117. Moreover the outlet tube 100 has a group of valves 118A-D corresponding to valves 117. Two different eluant solutions may be introduced into the system through conduits 119, 120 leading to connecting tubes 121 for a mixing chamber (not shown) the outlet of which communicates with eluent conduit 97. After the primary volume 89 has been filled in, the sample liquid can be directed to any one of the flow cells 11A-D with the aid of the eluent liquid, the valves 117 and 118 being maintained open and closed in appropriate combinations. For instance, if the sample solution is to be passed on to flow cell 11C, then valves 114A, B and D are kept closed, 110 closed, 117A and B open, 117C closed, 111, 118A and B closed, and 118C and D open. 115A, B and D should also be closed.

An especially advantageous feature of the liquid handling block unit according to FIG. 13 is that flow cells 11A-D can be coupled in series with each other. In that case one and the same sample liquid will pass through the flow cells one after the other. The number of such serially arranged flow cells may be 2, 3 or 4 depending on how the valves are set. For example, if all the four flow cells are to be coupled in series the following valves are maintained in the closed position when the eluent solution is forcing the sample solution out of the primary volume 89: Valves 110, 111, 113, 117A, 117C, 118B, 118D, 88; while the following are maintained in the open position: Valves 114A-D, 115A-D, 112, 90, 118A, 118C, 117B, 117D. The sample liquid and eluent solution run off to the waste disposal means via duct 116.

Another embodiment of the block unit for liquid handling is shown in FIGS. 14A, B and 15. This embodiment differs from that of FIG. 13 in that a secondary volume for liquid samples has been added and the liquid channel system has been duplicated. The secondary volume, which has an exactly defined volume, preferably different from that of the primary volume, can be coupled in series with the primary volume if and as desired. In this manner it thus becomes possible to analyze two sample liquid volumes which differ inter se and which both are well-defined. The duplicate channel system is a time-saving feature when analyses are carried out—for while the sample liquid of one channel system is being pumped into the flow cells for analysis the other channel system may at the same time be cleaned and filled with fresh sample liquid; so that when analysis of the sample liquid of the first channel system has been finalized the sample liquid of the second channel system is immediately ready and available for analysis.

The small rings in FIGS. 14 and 15 designate valves 201, 202, 203, 204, 205, 206, 207, 208A-B, 209A-C, 210A-B, 211, 212A-B, 214, 215. Furthermore, riser ducts are provided which are to be connected—via e.g. a block (not shown) having flexible tube connections and planar sealings around the riser duct ends on its underside—to the pump 96, to the pump (not shown) for sample liquid, to the sample solution waste disposal means 93, to the waste disposal means from the two channel systems and to the waste disposal means for sample solution plus eluent solution as shown to the right in the Figure, 101.

Valves having the same numeral in FIG. 15 are all controlled by one common compressed-air valve. Thus for instance, when valves 208 are pressurized, all the valves 208A, 208B, 208C and 208D are pressurized simultaneously.

If sample solution is to be pumped into the lowermost channel system of FIG. 15 then valves 209B, 214, 215, 209D and 213 are maintained in closed positions so that the sample liquid can pass through the open valves 208D to the primary volume 122 and thence to the secondary volume, designated by 123. If this secondary volume, too, is to be filled valve 213 is kept closed. Valves 212A and B are kept open, 209C closed, 208C open, the sample liquid being discharged via the waste disposal duct 124 of the lowermost channel system. When sample liquid in the primary and secondary volumes is to be analyzed, valves 208 are closed, valves 209 and 212 are opened, 213 is closed; and eluent solution is now pumped through the lower eluent channel 125 to force sample solution in the primary and secondary volumes through a desired flow cell 11A-D. Valves 201-207 serve as switch mechanisms for directing sample liquid to the desired flow cell. Sample and eluent solutions will then be discharged through an exhaust duct 126 which is common to both channel systems.

Correspondingly the uppermost channel system has an eluent channel 127 and a waste conduit 128, a primary volume 132 and a secondary volume 133.

Valves 208B and D, valves 209B and D, and valves 214, 215 serve as means for selecting the desired channel system, i.e. causing sample liquid to be pumped either into the lowermost channel system 135 or into the uppermost channel system 136. The sample liquid is pumped in through a common inlet channel 129.

In order to avoid sample carry-over, the T-section of the channel 129 can be washed. When the channel system 136 is washed, a small volume of the washing liquid is released through the waste disposal channel 130 by opening the valve 215 for a short time. When the channel system 135 is washed, a small volume of the washing liquid is released through the waste disposal channel 131 by opening the valve 214 for a short time.

Although not shown in FIGS. 14A, B and 15 the block unit for liquid handling may be provided with valves corresponding to valves 115, 18 in FIG. 13 to thus enable the flow cells to be coupled in series with one another.

By means of separating the valve functions so that every valve, i.e. also each of the valves 208A, 208B, 208C and 208D, is actuated by a separate compressed-air valve of its own, possibilities are provided to pump either the primary volume or the secondary volume, or the primary plus secondary volume, through a desired flow cell.

As may be seen from FIGS. 14A and 14B, the inlet channel 129 for sample liquid and the inlet channels 125, 127 for eluent solution all have a considerable length. This is so because the temperature is to be kept constant and equal in both of these solutions with the aid of the thermostat means 27 (shown in FIG. 2) which is situated below these channel portions and serves as a kind of a heat exchanger. The thermostat means 27 and thermostat means in housing 2 are both of the liquid-operated type, their liquid flows emanating preferably from one common liquid bath which is maintained under strict temperature control.

In the above-described embodiments of the invention a plurality of flow cells—up to 20—are arranged side by side and are irradiated simultaneously by a streak of light extending transversely over the flow cells and their sensing surfaces.

According to the invention it is also possible to employ just one flow cell the longitudinal direction of which is parallel to the streak of light, with a number of mutually spaced sensing surfaces which are arranged within the flow cell, are irradiated simultaneously by the light streak and are each functionalized in the manner described above. After functionalization in an apparatus with flow channels similar to that shown in FIG. 1 the sensing surfaces 40A–D are oriented as shown in FIG. 16. As will be seen from this Figure, the block unit for liquid handling 140 which is then used in the analysis phase may have just one single flow cell 141 instead of the four cells shown earlier. The chief advantage of such an arrangement resides in obtaining a short and well-defined interface between the sample liquid and eluent solution, as compared to the interface formed when the flow cells are coupled in series and the sample liquid travels along a winding path through the serial cells; in this case the interface tends to become elongated each bend of 180°.

From the above description of the block unit for liquid handling it will be evident that the number of primary volumes may be increased and that such additional volumes may each be given any size desired.

According to still another embodiment of the channel system in a liquid handling block unit of the type having a plurality of flow cells in side-by-side relationship, all the flow cells are simultaneously fed, each with one liquid of its own. In this manner the liquids can be analyzed simultaneously in the analytical apparatus. The liquids may be sample solutions of different types or of the same type. They may also be a number of sample solutions plus one or a plurality of reference solutions. This manner of parallelly analyzing a plurality of liquids is conducive to shortening the time required for analysis. Still another variant form of the invention resides in (i) providing a plurality of sensing surfaces in each of the flow cells lying next to each other side by side, and (ii) feeding all the flow cells simultaneously each with one liquid of its own. In this case the time required for analysis is shortened to a still greater extent, and a possibility is provided of qualitatively analyzing a greater number of substances simultaneously.

According to an alternative embodiment the layer 80 may be a plate of silicon into which slits extending therethrough and corresponding to the upwardly open channel portions 11A–D have been etched by means of a technique such as is known within the field of micromechanics.

Knowing the cross sectional area of the flow channel and also the volume capacity of the pump (e.g. in $\mu l$ per unit time) one is able to carry out a time-controlled pumping operation whereby a liquid volume chosen as desired is pumped along the sensing surfaces. Now looking at FIG. 15, suppose primary volume 122 has a capacity of 5 $\mu l$ and secondary volume 123 has a capacity of 45 $\mu l$: By means of opening valve 213 and closing valves 212A–B, alternatively opening valve 211 and close valves 210A–B, after a predetermined period of time corresponding to the desired liquid volume to be analyzed it is thus possible to feed any desired volume of between 5 and 50 $\mu l$ along a sensing surface.

Figure 1C:
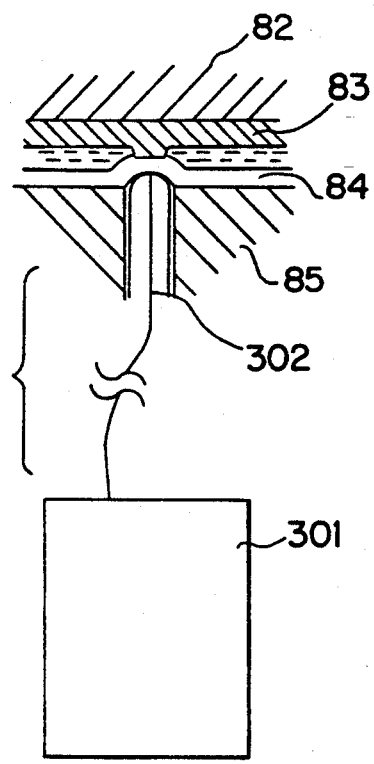

Solenoid-activated valves may be employed instead of the pneumatically activated valves. As illustrated in FIG. 1C, a solenoid-activated valve may consist, according to the invention, of a wire 302 of superelastic alloy attached to the solenoid armature. The wire extends through holes in the support plate into contact with the layer 84. When the solenoid 301 is activated the end of the wire 302 will push up the diaphragm 84 of the valve against the valve seat 105 in a similar way as shown in FIG. 1B. Typically the valve openings in the support plate 85 have a diameter of 0.5 mm; consequently the superelastic alloy wires 302 should have a diameter of an order of magnitude of 0.4 mm. Superelasticity in this case means that the wires 302 may be formed with sharp bends but nevertheless remain stiff.

FIG. 12 shows the region around plateau 81 of the block unit for liquid handling. As will be seen, there are a number of L-shaped angle pieces 101–105 on each side of the plateau for retaining carrier plate 42 in its position over the sheet 80.

It will be appreciated that when the analytical apparatus 18 is in its loading position, the housing being raised and the guide pins being retracted from openings 29, 30, a carrier plate 42 can be slid in between the L-shaped angle pieces 100–105. Then when the electric motor rotates and lowers its head the prism 4 in aperture 21 of housing 20 will be pressed against the opto-interface plate and thus also sensor unit 10 against layer 80 in a liquid-tight manner due to the weight of the housing. When the metal film 37 of the sensor unit 10 and the dielectric film 38 on metal film 37 are sealingly pressed against layer 80, flow cells will be created as formed by the aforesaid upwardly open portions 11A–D.

For initial calibration of the analytical apparatus, salt solutions each having a known refractive index are pumped one after the other past each of the sensing surfaces. The electric signals from the detectors of the photodetector columns corresponding to each of the sensing surfaces are stored in a memory, separately for each one of the salt solutions. By curve fitting of the response values from each of the photodetectors all the photodetector members of the analytical apparatus are calibrated so that a linear relationship is established between the salt concentrations and the measured refractive indices. Next, the sample solution is pumped through a flow channel 14 which serves as a reference channel; its sensing surface has no affinity for biomolecules at this particular time when the calibration is carried out. The electric signals obtained from the photodetector rows corresponding to the resonance angle of the sample solution are stored in another location of the memory. The purpose of this calibration is to determine the refractive index of the sample solution. The stored signal corresponding to that index is then corrected from the signals obtained when the sample solution is pumped through a flow channel with an activated sensing surface in order to determine a difference in refractive index due to the presence of the target biomolecule in the sample solution. The same reference channel may also be used for temperature monitoring of the analytical procedure; in case unnatural temperature variations are detected the pumps are stopped and analysis is discontinued.

By coating at least one of the sealing areas of layer 80 between the flow channels with a dielectricum of a suitable refractive index in order to gain SPR response, the temperature at layer 80 can be monitored. The refractive index of most organic materials is sensitive to temperature, and the dielectricum should have a known temperature dependence of its refractive index. Light beams reflected at the metal film 37 at areas thereof opposite to the film areas pressed in close optical contact with the liquid sealing areas of the dielectricum will be imaged by the anamorphic lens system 6 onto corresponding columns of detector elements, e.g. situated between columns of detector elements corresponding to flow channels. The electrical signal representing the resonance angle as measured at the sealing areas between the flow channels will represent an actual temperature value at the dielectric layer. By guidance from the measured difference between the corrected signal and the actual value, the thermostat system can be controlled towards the temperature set point selected. The measured electric signal may also, as an alternative, or complement, to the above described method, be used to correct for the baseline drift caused by temperature disturbances due to the thermostat means not being positioned in the flow cell.

The optical biosensor system instrument schematically described for a surface plasmon resonance detection in FIGS. 1 and 8, may also be adapted for detection using critical angle refractometry, multiple angle evanescent wave ellipsometry, and Brewster angle reflectometry, in that the first lens means 62 and the second lens means 65 are generally similar for these various detection principles. It should be noted, however, that the addition of specific optical components are required for the employment of ellipsometry in the optical biosensor system.

Additionally, the optical biosensor system instrument described in FIGS. 1 and 8, may be arranged for employing variable angle total internal reflection fluorescence, variable angle total internal reflection phosphorescence, variable angle total internal reflection light scattering. More specifically, the second lens means 65 may be positioned for detection of in-line fluorescence or phosphorescence, or as indicated in FIG. 1, by the second lens means 165 and photodetectors 161 for detection of right-angle fluorescence or phosphorescence, or of right angle light scattering.

The above-described embodiments of the invention may be modified and varied in many ways within the scope of the inventive concept.

We claim:

1. An optical biosensor system using an internal reflection versus angle of incidence determination for detecting a specific biomolecule, comprising:
   a sensor unit including a transparent plate, at least a portion of one of the faces of said plate having a dielectric film adhered thereto, or being primarily coated with a metal film to which has been adhered a dielectric film, said dielectric film having an affinity for the specific biomolecule at the time the measurement is carried out;
   a light source, including first lens means, for directing a beam of light at an interface of the transparent plate and said metal film or said dielectric film directly adhered thereto to produce an evanescent wave at a sensing surface of said dielectric film when a sample solution contacts said dielectric film on the transparent plate;
   optical imaging instrumentation including second lens means by which one of light reflected from said sensing surface of the transparent plate, light originating from the sample through evanescent wave stimulated fluorescence or phosphorescence, and light originating from scattering at said sensing surface, is imaged on a photodetector device; and
   an evaluation unit for determining at least one of an angle of minimum reflectance, a state of polarization, and a collected light intensity;
   wherein at least one sensing surface is arranged on the sensor unit;
   wherein said at least one sensing surface, in order to form an elongated flow cell, is pressed over an upwardly open portion of at least one channel for the sample solution which is to be analyzed and affects at least one of the angle of minimum reflectance, the polarization state for minimum reflectance, and the collected light intensity, at which the evanescent wave interacts with the sample;
   wherein said first lens means forms a convergent beam of light focused in a wedge-shape fashion to form a streak of light extending transversely over all of said at least one sensing surface;
   wherein the photodetector device, at least in the case of more than one sensing surface, is a two-dimensional matrix of individual photodetectors;
   wherein said second lens means is a lens system for imaging rays of one of said reflected light from said at least one sensing surface, said light emitted from the sample, and said light originating from scattering at the sensing surface onto a corresponding column of photodetectors, so that said at least one sensing surface has at least one corresponding column of photodetectors;
   wherein said evaluation unit determines at least one of the angle of minimum reflectance, the state of polarization, and the collected light intensity, for said at least one sensing surface.

2. The optical biosensor system of claim 1, further comprising:
   a support in which the open portion of the at least one channel is arranged in a fixed position;
   a housing in which said light source, said optical imaging instrumentation, the photodetector device, and a coupling prism are arranged in fixed positions;
   an aperture provided in said housing below said coupling prism and covered by an opto-interface plate for coupling incident and reflected light and/or scattered or emitted light from the sample, respectively, to said sensor unit and said optical imaging instrumentation; and
   holder means by which said sensor unit is detachably attached below said aperture,
   said housing being placed on top of said sensor unit for pressing the opto-interface plate against an opposite face of said sensor unit.

3. The optical biosensor system of claim 2, wherein said housing is hinged to said support by means of a system of articulated arms extending from each lateral face of said housing and said support, respectively.

4. The optical biosensor system of claim 2, further comprising thermostat means provided in said housing and at the at least one channel, for thermostatically controlling said at least one sensing surface and the at least one channel, respectively.

5. The optical biosensor system of claim 1, wherein said at least one sensing surface includes a plurality of sensing surfaces, arranged in a side-by-side relationship on said sensor unit.

6. The optical biosensor system of claim 1, wherein the transparent plate of said sensor unit is of glass.

7. The optical biosensor system of claim 1, wherein the dielectric film comprises a dextran layer.

8. The optical biosensor system of claim 1 wherein the at least one channel includes a plurality of channels arranged in a parallel side-by-side relationship, wherein each of the plurality of channels has a corresponding upwardly open portion, wherein the corresponding upwardly open portions are all covered by said sensor unit when a measurement is performed, and wherein in said measuring stage, wherein each of said at least one sensing surfaces is situated above its corresponding upwardly open portion.

9. The optical biosensor system of claim 8, wherein each of the corresponding upwardly open portions are slits extending through a first layer of elastomer material or silicon.

10. The optical biosensor system of claim 9, wherein the first layer is made of a rubber material.

11. The optical biosensor system of claim 10, wherein said plurality of channels are formed in a liquid handling block unit of a solid material selected from the group consisting of plastics, metals and ceramics.

12. The optical biosensor system of claim 8 wherein means are provided which permit said plurality of channels to be coupled in series with each other.

13. The optical biosensor system of claim 9, wherein said plurality of channels are formed in a liquid handling block unit of a solid material selected from the group consisting of plastic, metal, and ceramics, and wherein said liquid handling block unit comprises:
 a planar support plate having a second elastomer layer on its upper face;
 a base plate positioned on top of the second elastomer layer including,
 a third elastomer layer positioned on an underside of said base plate,
 a first number of riser ducts which correspond to a number of the corresponding upwardly open channel portions, extend through said base plate, and connect with one end of each of the corresponding upwardly open channel portions, and
 a second number of riser ducts which correspond to the number of corresponding upwardly open channel portions and connect with an opposite end of each of the corresponding upwardly open channel portions;
 a pattern of channels formed in the third elastomer layer including,
 at least one primary volume for a sample liquid, said primary volume having a first exactly determined volume,
 at least one inlet channel for said sample liquid,
 at least one inlet channel for eluent liquid, and
 an outlet channel for said sample and eluent liquids; and
 a plurality of individually controllable valve means in said planar support plate for directing the liquid flow in said plurality of channels.

14. The optical biosensor system of claim 13, further comprising a secondary volume for said sample liquid, said secondary volume having a second exactly determined volume which differs from said first exactly determined volume.

15. The optical biosensor system of claim 14, further comprising a second plurality of channels so that said second plurality of channels are filled while said sample liquid of said plurality of channels is analyzed.

16. The optical biosensor system of 13, wherein pneumatic valves are formed in through openings in said planar support plate, by the second elastomer layer above these through openings, and by valve seats in the form of projections from the third elastomer layer of said base plate.

17. The optical biosensor system of claim 13, wherein each of said plurality of individually controllable valve means comprise solenoids actuating respective wires, each wire being of superelastic material and extending through the through opening in said support plate to act upon the second elastomer layer.

18. The optical biosensor system of claim 8, wherein the corresponding upwardly open portions have a length of about 800 $\mu$m, a width of about 300 $\mu$m, and a height of about 30 $\mu$m.

19. The optical biosensor system of claim 2, further comprising:
 a carrier plate for said sensor unit, wherein an opening in said carrier plate accommodates said sensor unit and wherein said sensor unit rests on flange means at a lower end of said opening.

20. The optical biosensor system of claim 1, wherein said second lens means is an anamorphic second lens system for
 imaging reflected rays of light from surface elements in a longitudinal direction of the streak of light, in the form of real image elements corresponding to rows and columns of photodetectors where each column corresponds to part of said at least one sensing surface in a direction of the streak of light, and
 imaging reflected rays of light from surface elements transverse to the longitudinal direction of the streak of light, onto pixels situated along the columns of photodetectors, such that mutually parallel incident rays lying in a plane of incidence and aligned transversely to the longitudinal direction of the streak of light are focused toward a single photodetector in a column, so that each detector in a column corresponds to a one particular angle of incidence.

21. The optical biosensor system of claim 20, wherein said internal reflection versus angle of incidence determination is based upon surface plasmon resonance.

22. The optical biosensor system of claim 21, wherein a convergent beam of light strikes a reverse side of the metal film with angles of incidence of between 62 and 78 degrees.

23. The optical biosensor system of claim 1, wherein said second lens means is arranged for collecting one of rays of light emitted from a sample and rays of light scattered from surface elements in a longitudinal direction of the streak of light, onto columns of photodetectors where each column corresponds to part of said at least one sensing surface in the direction of the streak of light, and for
 collecting rays of light from surface elements transverse to the longitudinal direction of the streak of light, onto pixels situated along the columns of photodetectors, such that mutually parallel incident rays lying in a plane of incidence and aligned transverse to the longitudinal direction of the streak of light are focused toward a single photodetector in a column, so that each photodetector in a column corresponds to one particular angle of incidence.

24. The optical biosensor system of claim 1, wherein said at least one sensing surface includes a plurality of surfaces, a width of the streak of light irradiating said plurality of sensing surface is substantially equal to an extent of said plurality of sensing surfaces transverse to the longitudinal direction of the streak of light to produce an integrated mean value of a mass of biomolecules binding to the dielectric film transverse to the longitudinal direction of the streak of light, thereby permitting a reproducible quantitative analysis or alternatively a reproducible analysis of the relative amount of the particular biomolecule.

25. The optical biosensor system of claim 24, wherein an extent of said plurality of sensing surfaces in the longitudinal direction of the streak of light are imaged in reduced size on a single photodetector, to produce an integrated mean value of the mass of biomolecules binding to the dielectric film in the longitudinal direction of the streak of light.

26. The optical biosensor system of claim 20, wherein said second lens means reduces an image element in S planes with a linear degree of magnification m=0.56 when the extent is of the order of magnitude of about 300 μm and the photodetector has dimensions of about 90×90 μm.

27. The optical biosensor system of claim 1, wherein said first lens means of said light source includes a lens member for varying the width of the streak of light irradiating each of said at least one sensing surfaces.

28. The optical biosensor system of claim 2, wherein said coupling prism is a truncated straight hemicylinder placed over said aperture in a bottom wall of the housing.

29. The optical biosensor system of claim 22, wherein said light source in combination with a filter emits substantially monochromatic and incoherent light.

30. The optical biosensor system of claim 22, wherein said light source emits substantially monochromatic and coherent light.

31. The optical biosensor system of claim 2, further comprising positioning means for determining relative positions of said housing, said sensor unit and said support.

32. The optical biosensor system of claim 2 wherein said opto-interface plate includes,
a second transparent plate of glass including longitudinally extending parallel ridges on one face aligned with longitudinally extending parallel ridges on an opposite face of said second transparent plate, said ridges being made of an elastic transparent material, spaced apart with distances between corresponding to distances between each of said at least one sensing surfaces with a length at least sufficient to couple an entire cross section of the convergent beam of light to said sensor unit and pressed against said transparent plate of said sensor unit directly opposite each of said at least one sensing surfaces.

33. The optical biosensor system of claim 32, wherein each of said longitudinally extending parallel ridges has a number of longitudinally extending stepped portions on each side to form a structure having, in cross section, a configuration of a flight of stairs, the uppermost steps thereof being pressed resiliently against said sensor unit and said coupling prism without formation of enclosed air pockets.

34. The optical biosensor system of claim 23, wherein said evaluation unit is arranged such that when the mass of bound specific biomolecules is calculated, the calculation includes light emitted from samples or scattered from said at least one sensing surface from only a partial band of the width of said at least one sensing surface and positioned centrally therein, this positioning being effectuated by evaluation of electric signals obtained from the photodetectors in a column which corresponds to a corresponding partial band on each of said at least one sensing surface.

35. The optical biosensor system of claim 25, wherein said evaluation unit is arranged such that when the mass of bound specific biomolecules is calculated, the calculation includes reflected light from only a narrow band.

36. The optical biosensor system of claim 35, wherein said evaluation unit is arranged for calculating parameters for a surface plasmon resonance curve for a determination including a reflectance minimum and a resonance angle and a displacement thereof for each flow cell, by curve fitting response values obtained from column detector members corresponding to the resonance angle.

37. The optical biosensor system of claim 2, wherein said coupling prism is a plane-sided prism placed over the aperture in a bottom wall of said housing, wherein refractive properties of said plane-sided prism determine a layout of said first lens means in order to form a convergent beam of light focused in a wedge-shaped fashion into the streak of light extending transversely over all sensitized areas.

38. The optical biosensor system of claim 37, wherein the upwardly open channel portion of at least one channel is a wall-jet cell, from which a jet flow is directed against a centre of a circular sensing surface.

39. A method of calibrating the optical biosensor system of claim 1, comprising the steps of:
directing a beam of light from said light source to form a streak of light extending transversely over all of said at least one sensing surface;
pumping a plurality of calibration solutions without affinity to said at least one sensing surface, each with a known refractive index one after the other, through a flow cell,
storing electric signals from the detectors of the photodetector rows corresponding to said at least one sensing surface in a memory, for each of the plurality of calibration solutions, so that a known relationship is obtained between a resonance angle and a refractive index of the dielectric film, and
calibrating the response from each of the photodetector rows.

40. The method of claim 39, further comprising the steps of:
passing the sample solution over a separate sensing surface that has no affinity for any biomolecule and is situated on said metal film;
storing the electric signals obtained from the photodector rows corresponding to the separate, non-affinity sensing surface in another location of the memory;
and correcting the stored signals obtained when the sample solution is passed along said at least one sensing surface, to determine a difference between the refractive indices due to the presence of the particular biomolecule for said at least one sensing surface.

41. A method of correcting for baseline drift in surface plasmon resonance (SPR) analysis procedures using the optical biosensor system of claim 1, comprising the steps of:
    establishing a predetermined temperature set point for the sample solution;
    creating an electric signal representing an actual temperature value of the sample solution, by utilizing electric signals which represent the resonance angle as measured in a flow cell, a sensing surface of which has no affinity for the specific molecule and through which a liquid is fed which is conveyed through a liquid flow handling unit;
    correcting the signals from the sample solution with respect to a temperature disturbance caused by not positioning a thermostat in the flow cell; and
    controlling said thermostat by measuring difference between the corrected signal and the actual value in order to adjust the temperature set point.

42. A method of measuring the actual feedback value of the temperature at the flow channels for regulation of a thermostat system by surface plasmon resonance (SPR) analysis procedures using the optical biosensor system of claim 1 comprising the steps of:
    creating an electrical signal representing an actual temperature value of the sample solution, by utilizing electric signals which represent the resonance angle as measured at a flow cell, a sensing surface of which is in contact with at least one sealing area adjacent or between the flow channels, wherein said sealing area is coated with a dielectricum of suitable material and refractive index properties in order to obtain a surface plasmon resonance (SPR) response from said sealing area, said dielectricum having a known temperature dependence of its refractive index, light beams reflected at areas of the metal film opposite to areas of the film pressed in close optical contact with the liquid sealing areas of said dielectricum being imaged by the second lens means, being anamorphic onto corresponding columns of detector elements; and
    controlling said thermostat system by measuring a difference between the corrected signal and the actual value in order to adjust the temperature toward the temperature set point.

43. The optical biosensor system of claim 1, wherein said optical imaging instrumentation further including optical filter means.

44. The optical biosensor system of claim 10, wherein the rubber material is silicon rubber.

45. The optical biosensor system of claim 29, wherein said light source includes a light emitting diode and a interference filter.

46. The optical biosensor system of claim 30, wherein said light source includes one of a semiconductor diode laser, a dye laser, and a gas laser.

47. The optical biosensor system of claim 36, wherein the response values are curve fitted using a reflectance minimum of the resonance angle.

48. The optical biosensor system of claim 1, wherein said at least one sensing surface includes a plurality of surfaces, a width of the streak of light irradiating said plurality of sensing surfaces is substantially equal to an extent of said plurality of sensing surfaces transverse to the longitudinal direction of the streak of light to produce an integrated mean value of a mass of biomolecules binding to the dielectric film transverse to the longitudinal direction of the streak of light, thereby permitting a reproducible quantitative analysis or alternatively a reproducible analysis of the relative amount of the particular biomolecule.

49. The optical biosensor system of claim 43, wherein an extent of each of said at least one sensing surfaces in the longitudinal direction of the streak of light are imaged in reduced size on a single photodetector, to produce an integrated mean value of the mass of biomolecules binding to the dielectric film in the longitudinal direction of the streak of light.

50. The optical biosensor system of claim 1, wherein said second lens means is an anamorphic lens system for imaging rays of reflected light from said at least one sensing surface, and said evanescent wave is produced by surface plasmon resonance.

51. The optical biosensor system of claim 1, wherein said second lens means is a lens system for imaging one of rays of light emitted from the sample and rays scattered at the sensing surface, said emission and said scattering of said light rays being generated by said evanescent wave.

52. The optical biosensor system of claim 35, wherein said narrow band is preferably about 50% of the width of each of said plurality of sensing surfaces, said narrow band extending substantially along an entire length of each of said plurality of sensing surfaces and positioned centrally therein, this positioning being effectuated by evaluation of electric signals obtained from the photodetectors in a column which corresponds to a corresponding narrow band on each of said plurality of sensing surfaces.

53. The method of claim 39, wherein said plurality of calibration solutions are salt solutions and/or suitable organic solutions.

* * * * *

UNITED STATES PATENT AND TRADEMARK OFFICE
CERTIFICATE OF CORRECTION

PATENT NO. : 5,313,264
DATED : May 17, 1994
INVENTOR(S) : Ivarsson et al.

It is certified that error appears in the above-indentified patent and that said Letters Patent is hereby corrected as shown below:

On the title page: Item [75]

Change second Inventor's name from "Jönsson Ulf" to --Ulf Jönsson--

Change residences of second, third, and fourth Inventors from "Upsala" to --Uppsala--

Change the address of the Assignee from "Upsala, Sweden" to --Uppsala, Sweden--

Signed and Sealed this

Sixteenth Day of August, 1994

Attest:

BRUCE LEHMAN

Attesting Officer   Commissioner of Patents and Trademarks

UNITED STATES PATENT AND TRADEMARK OFFICE
CERTIFICATE OF CORRECTION

| | |
|---|---|
| PATENT NO. | : 5,313,264 |
| APPLICATION NO. | : 07/681533 |
| DATED | : May 17, 1994 |
| INVENTOR(S) | : Bengt Ivarsson et al. |

It is certified that error appears in the above-identified patent and that said Letters Patent is hereby corrected as shown below:

On the Title Page
Item (30)
Foreign Application Priorty Data "Nov. 10, 1988 [CH] Switzerland....... 8804075-3"
should read as -- Nov. 10, 1988 [SE] Sweden....... 8804075-3--

Signed and Sealed this

First Day of May, 2007

JON W. DUDAS
*Director of the United States Patent and Trademark Office*